(12) United States Patent
Stafford

(10) Patent No.: US 8,613,892 B2
(45) Date of Patent: Dec. 24, 2013

(54) ANALYTE METER WITH A MOVEABLE HEAD AND METHODS OF USING THE SAME

(75) Inventor: Gary Ashley Stafford, Hayward, CA (US)

(73) Assignee: Abbott Diabetes Care Inc., Alameda, CA (US)

( * ) Notice: Subject to any disclaimer, the term of this patent is extended or adjusted under 35 U.S.C. 154(b) by 1079 days.

(21) Appl. No.: 12/495,801

(22) Filed: Jun. 30, 2009

(65) Prior Publication Data

US 2010/0331653 A1    Dec. 30, 2010

(51) Int. Cl.
*G01N 35/00* (2006.01)

(52) U.S. Cl.
USPC ............. 422/403; 422/50; 422/400; 422/401; 422/402; 422/408; 422/410

(58) Field of Classification Search
USPC ............ 422/50, 400, 401, 402, 403, 408, 410
See application file for complete search history.

(56) References Cited

U.S. PATENT DOCUMENTS

| | | |
|---|---|---|
| 3,123,790 A | 3/1964 | Tyler |
| 3,581,062 A | 5/1971 | Aston |
| 3,926,760 A | 12/1975 | Allen et al. |
| 3,949,388 A | 4/1976 | Fuller |
| 4,036,749 A | 7/1977 | Anderson |
| 4,040,547 A | 8/1977 | Dickey |
| 4,055,175 A | 10/1977 | Clemens et al. |
| 4,129,128 A | 12/1978 | McFarlane |
| 4,245,634 A | 1/1981 | Albisser et al. |
| 4,327,725 A | 5/1982 | Cortese et al. |
| 4,344,438 A | 8/1982 | Schultz |
| 4,349,728 A | 9/1982 | Phillips et al. |
| 4,373,527 A | 2/1983 | Fischell |
| 4,411,267 A | 10/1983 | Heyman |
| 4,419,794 A | 12/1983 | Horton et al. |
| 4,425,920 A | 1/1984 | Bourland et al. |
| 4,478,976 A | 10/1984 | Goertz et al. |
| 4,494,950 A | 1/1985 | Fischell |
| 4,509,531 A | 4/1985 | Ward |
| 4,514,276 A | 4/1985 | Covington et al. |
| 4,527,240 A | 7/1985 | Kvitash |
| 4,538,616 A | 9/1985 | Rogoff |
| 4,619,793 A | 10/1986 | Lee |
| 4,671,288 A | 6/1987 | Gough |
| 4,685,466 A | 8/1987 | Rau |
| 4,703,756 A | 11/1987 | Gough et al. |

(Continued)

FOREIGN PATENT DOCUMENTS

| | | |
|---|---|---|
| DE | 4401400 | 7/1995 |
| EP | 0098592 | 1/1984 |

(Continued)

OTHER PUBLICATIONS

*American Heritage Dictionary*, 4th ed., Houghton Mifflin Company, 2000, pp. 782.

(Continued)

*Primary Examiner* — Monique Cole
(74) *Attorney, Agent, or Firm* — Jackson & Co., LLP

(57) ABSTRACT

The present disclosure provides in vitro analyte meters that include a meter portion that is moveable relative to at least one other meter portion. Embodiments include moveable meters that are integrated with in vivo analyte systems. Also provided are methods, systems and kits.

18 Claims, 4 Drawing Sheets

(56) References Cited

U.S. PATENT DOCUMENTS

| | | |
|---|---|---|
| 4,711,247 A | 12/1987 | Fishman |
| 4,729,672 A | 3/1988 | Takagi |
| 4,731,726 A | 3/1988 | Allen, III |
| 4,749,985 A | 6/1988 | Corsberg |
| 4,757,022 A | 7/1988 | Shults et al. |
| 4,777,953 A | 10/1988 | Ash et al. |
| 4,779,618 A | 10/1988 | Mund et al. |
| 4,854,322 A | 8/1989 | Ash et al. |
| 4,890,620 A | 1/1990 | Gough |
| 4,895,147 A | 1/1990 | Bodicky et al. |
| 4,925,268 A | 5/1990 | Iyer et al. |
| D310,167 S | 8/1990 | Reber |
| 4,953,552 A | 9/1990 | DeMarzo |
| 4,986,271 A | 1/1991 | Wilkins |
| 4,988,341 A | 1/1991 | Columbus et al. |
| 4,995,402 A | 2/1991 | Smith et al. |
| 5,000,180 A | 3/1991 | Kuypers et al. |
| 5,002,054 A | 3/1991 | Ash et al. |
| 5,013,161 A | 5/1991 | Zaragoza et al. |
| 5,019,974 A | 5/1991 | Beckers |
| 5,050,612 A | 9/1991 | Matsumura |
| 5,054,170 A | 10/1991 | Otrusina |
| 5,055,171 A | 10/1991 | Peck |
| 5,082,550 A | 1/1992 | Rishpon et al. |
| 5,106,365 A | 4/1992 | Hernandez |
| 5,122,925 A | 6/1992 | Inpyn |
| 5,140,985 A | 8/1992 | Schroeder et al. |
| 5,165,407 A | 11/1992 | Wilson et al. |
| 5,201,858 A | 4/1993 | Otrusina |
| 5,238,729 A | 8/1993 | Debe |
| 5,246,867 A | 9/1993 | Lakowicz et al. |
| 5,262,035 A | 11/1993 | Gregg et al. |
| 5,262,305 A | 11/1993 | Heller et al. |
| 5,264,104 A | 11/1993 | Gregg et al. |
| 5,264,105 A | 11/1993 | Gregg et al. |
| 5,279,294 A | 1/1994 | Anderson et al. |
| 5,285,792 A | 2/1994 | Sjoquist et al. |
| 5,293,877 A | 3/1994 | O'Hara et al. |
| 5,299,571 A | 4/1994 | Mastrototaro |
| 5,320,725 A | 6/1994 | Gregg et al. |
| 5,322,063 A | 6/1994 | Allen et al. |
| D348,355 S | 7/1994 | Scheid et al. |
| 5,340,722 A | 8/1994 | Wolfbeis et al. |
| 5,342,789 A | 8/1994 | Chick et al. |
| 5,356,786 A | 10/1994 | Heller et al. |
| 5,360,404 A | 11/1994 | Novacek et al. |
| 5,370,622 A | 12/1994 | Livingston et al. |
| 5,372,427 A | 12/1994 | Padovani et al. |
| 5,379,238 A | 1/1995 | Stark |
| 5,385,282 A | 1/1995 | Chen |
| 5,390,671 A | 2/1995 | Lord et al. |
| 5,391,250 A | 2/1995 | Cheney, II et al. |
| 5,408,999 A | 4/1995 | Singh et al. |
| 5,411,647 A | 5/1995 | Johnson et al. |
| 5,431,160 A | 7/1995 | Wilkins |
| 5,431,921 A | 7/1995 | Thombre |
| 5,452,497 A | 9/1995 | Peng |
| 5,462,645 A | 10/1995 | Albery et al. |
| 5,472,317 A | 12/1995 | Field et al. |
| D366,957 S | 2/1996 | Scheid et al. |
| 5,489,414 A | 2/1996 | Schreiber et al. |
| 5,497,772 A | 3/1996 | Schulman et al. |
| 5,507,288 A | 4/1996 | Bocker et al. |
| 5,509,410 A | 4/1996 | Hill et al. |
| 5,514,718 A | 5/1996 | Lewis et al. |
| 5,531,878 A | 7/1996 | Vadgama et al. |
| 5,568,806 A | 10/1996 | Cheney, II et al. |
| 5,569,186 A | 10/1996 | Lord et al. |
| 5,582,184 A | 12/1996 | Erickson et al. |
| 5,584,813 A | 12/1996 | Livingston et al. |
| 5,586,553 A | 12/1996 | Halili et al. |
| 5,593,852 A | 1/1997 | Heller et al. |
| 5,601,435 A | 2/1997 | Quy |
| 5,609,575 A | 3/1997 | Larson et al. |
| 5,613,236 A | 3/1997 | Tajima et al. |
| 5,620,120 A | 4/1997 | Tien |
| 5,628,310 A | 5/1997 | Rao et al. |
| 5,632,557 A | 5/1997 | Simons |
| 5,653,239 A | 8/1997 | Pompei et al. |
| 5,665,222 A | 9/1997 | Heller et al. |
| 5,709,012 A | 1/1998 | Ebashi |
| 5,711,001 A | 1/1998 | Bussan et al. |
| 5,711,861 A | 1/1998 | Ward et al. |
| 5,733,044 A | 3/1998 | Rose et al. |
| 5,735,285 A | 4/1998 | Albert et al. |
| 5,749,656 A | 5/1998 | Boehm et al. |
| 5,766,131 A | 6/1998 | Kondo et al. |
| 5,772,586 A | 6/1998 | Heinonen et al. |
| 5,791,344 A | 8/1998 | Schulman et al. |
| 5,806,146 A | 9/1998 | Chen |
| 5,807,375 A | 9/1998 | Gross et al. |
| 5,850,954 A | 12/1998 | Dong-Joo |
| 5,851,197 A | 12/1998 | Marano et al. |
| D408,878 S | 4/1999 | Patten |
| D409,374 S | 5/1999 | Laba et al. |
| 5,899,855 A | 5/1999 | Brown |
| 5,906,031 A | 5/1999 | Jensen |
| 5,925,021 A | 7/1999 | Castellano et al. |
| 5,942,979 A | 8/1999 | Luppino |
| 5,948,006 A | 9/1999 | Mann |
| 5,957,854 A | 9/1999 | Besson et al. |
| 5,961,451 A | 10/1999 | Reber et al. |
| 5,964,993 A | 10/1999 | Blubaugh, Jr. et al. |
| 5,965,380 A | 10/1999 | Heller et al. |
| 5,971,922 A | 10/1999 | Arita et al. |
| 5,988,577 A | 11/1999 | Phillips et al. |
| 5,995,860 A | 11/1999 | Sun et al. |
| D418,119 S | 12/1999 | Rowell |
| 6,001,067 A | 12/1999 | Shults et al. |
| 6,022,368 A | 2/2000 | Gavronsky et al. |
| 6,024,699 A | 2/2000 | Surwit et al. |
| 6,026,321 A | 2/2000 | Miyata et al. |
| 6,027,459 A | 2/2000 | Shain et al. |
| 6,049,727 A | 4/2000 | Crothall |
| 6,059,156 A | 5/2000 | Lehtinen |
| 6,068,399 A | 5/2000 | Tseng |
| 6,083,710 A | 7/2000 | Heller et al. |
| 6,088,608 A | 7/2000 | Schulman et al. |
| 6,091,975 A | 7/2000 | Daddona et al. |
| 6,091,976 A | 7/2000 | Pfeiffer et al. |
| 6,093,172 A | 7/2000 | Funderburk et al. |
| 6,103,033 A | 8/2000 | Say et al. |
| 6,105,923 A | 8/2000 | Robertson et al. |
| 6,117,290 A | 9/2000 | Say et al. |
| 6,119,028 A | 9/2000 | Schulman et al. |
| 6,120,676 A | 9/2000 | Heller et al. |
| 6,121,009 A | 9/2000 | Heller et al. |
| 6,121,611 A | 9/2000 | Lindsay et al. |
| 6,122,351 A | 9/2000 | Schlueter, Jr. et al. |
| 6,134,461 A | 10/2000 | Say et al. |
| 6,159,147 A | 12/2000 | Lichter et al. |
| 6,162,611 A | 12/2000 | Heller et al. |
| 6,175,752 B1 | 1/2001 | Say et al. |
| 6,176,401 B1 | 1/2001 | Lim |
| 6,200,265 B1 | 3/2001 | Walsh et al. |
| 6,212,416 B1 | 4/2001 | Ward et al. |
| 6,219,574 B1 | 4/2001 | Cormier et al. |
| 6,248,067 B1 | 6/2001 | Causey, III et al. |
| 6,254,536 B1 | 7/2001 | DeVito |
| 6,275,717 B1 | 8/2001 | Gross et al. |
| 6,283,348 B1 | 9/2001 | Wang |
| 6,283,761 B1 | 9/2001 | Joao |
| 6,283,982 B1 | 9/2001 | Levaughn et al. |
| 6,284,478 B1 | 9/2001 | Heller et al. |
| 6,293,925 B1 | 9/2001 | Safabash et al. |
| 6,293,962 B1 | 9/2001 | Bishay |
| 6,295,506 B1 | 9/2001 | Heinonen et al. |
| 6,306,104 B1 | 10/2001 | Cunningham et al. |
| 6,309,884 B1 | 10/2001 | Cooper et al. |
| 6,329,161 B1 | 12/2001 | Heller et al. |
| 6,348,640 B1 | 2/2002 | Navot et al. |
| 6,359,444 B1 | 3/2002 | Grimes |
| 6,360,888 B1 | 3/2002 | McIvor et al. |
| 6,366,794 B1 | 4/2002 | Moussy et al. |

(56) References Cited

U.S. PATENT DOCUMENTS

| | | |
|---|---|---|
| 6,368,141 B1 | 4/2002 | Van Antwerp et al. |
| 6,377,828 B1 | 4/2002 | Chaiken et al. |
| 6,379,301 B1 | 4/2002 | Worthington et al. |
| D457,308 S | 5/2002 | Infanti |
| 6,424,847 B1 | 7/2002 | Mastrototaro et al. |
| 6,427,088 B1 | 7/2002 | Bowman, IV et al. |
| 6,437,679 B1 | 8/2002 | Roques |
| 6,440,068 B1 | 8/2002 | Brown et al. |
| 6,443,340 B1 | 9/2002 | Chung et al. |
| 6,470,535 B1 | 10/2002 | Mayne et al. |
| 6,478,736 B1 | 11/2002 | Mault |
| 6,484,046 B1 | 11/2002 | Say et al. |
| 6,514,718 B2 | 2/2003 | Heller et al. |
| 6,520,326 B2 | 2/2003 | McIvor et al. |
| 6,522,927 B1 | 2/2003 | Bishay et al. |
| 6,551,494 B1 | 4/2003 | Heller et al. |
| 6,558,320 B1 | 5/2003 | Causey, III et al. |
| 6,558,321 B1 | 5/2003 | Burd et al. |
| 6,560,471 B1 | 5/2003 | Heller et al. |
| 6,561,978 B1 | 5/2003 | Conn et al. |
| 6,562,001 B2 | 5/2003 | Lebel et al. |
| 6,564,105 B2 | 5/2003 | Starkweather et al. |
| 6,565,509 B1 | 5/2003 | Say et al. |
| 6,571,128 B2 | 5/2003 | Lebel et al. |
| 6,572,566 B2 | 6/2003 | Effenhauser |
| 6,576,101 B1 | 6/2003 | Heller et al. |
| 6,577,899 B2 | 6/2003 | Lebel et al. |
| 6,579,690 B1 | 6/2003 | Bonnecaze et al. |
| 6,585,644 B2 | 7/2003 | Lebel et al. |
| 6,589,229 B1 | 7/2003 | Connelly et al. |
| 6,591,125 B1 | 7/2003 | Buse et al. |
| 6,595,919 B2 | 7/2003 | Berner et al. |
| 6,605,200 B1 | 8/2003 | Mao et al. |
| 6,605,201 B1 | 8/2003 | Mao et al. |
| 6,607,509 B2 | 8/2003 | Bobroff et al. |
| 6,610,012 B2 | 8/2003 | Mault |
| 6,633,772 B2 | 10/2003 | Ford et al. |
| 6,635,014 B2 | 10/2003 | Starkweather et al. |
| 6,648,821 B2 | 11/2003 | Lebel et al. |
| 6,654,625 B1 | 11/2003 | Say et al. |
| 6,659,948 B2 | 12/2003 | Lebel et al. |
| 6,668,196 B1 | 12/2003 | Villegas et al. |
| 6,676,290 B1 | 1/2004 | Lu |
| 6,687,546 B2 | 2/2004 | Lebel et al. |
| 6,689,056 B1 | 2/2004 | Kilcoyne et al. |
| 6,694,191 B2 | 2/2004 | Starkweather et al. |
| 6,695,860 B1 | 2/2004 | Ward et al. |
| 6,702,857 B2 | 3/2004 | Brauker et al. |
| 6,733,446 B2 | 5/2004 | Lebel et al. |
| 6,740,075 B2 | 5/2004 | Lebel et al. |
| 6,741,877 B1 | 5/2004 | Shults et al. |
| 6,746,582 B2 | 6/2004 | Heller et al. |
| 6,752,299 B2 | 6/2004 | Shetler et al. |
| 6,758,810 B2 | 7/2004 | Lebel et al. |
| 6,770,030 B1 | 8/2004 | Schaupp et al. |
| 6,790,178 B1 | 9/2004 | Mault et al. |
| 6,809,653 B1 | 10/2004 | Mann et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,813,519 B2 | 11/2004 | Lebel et al. |
| 6,849,052 B2 | 2/2005 | Ughigaki et al. |
| 6,854,882 B2 | 2/2005 | Chen |
| 6,862,465 B2 | 3/2005 | Shults et al. |
| 6,873,268 B2 | 3/2005 | Lebel et al. |
| 6,881,551 B2 | 4/2005 | Heller et al. |
| 6,892,085 B2 | 5/2005 | McIvor et al. |
| 6,895,265 B2 | 5/2005 | Silver |
| 6,931,327 B2 | 8/2005 | Goode, Jr. et al. |
| 6,932,894 B2 | 8/2005 | Mao et al. |
| 6,936,006 B2 | 8/2005 | Sabra |
| 6,942,518 B2 | 9/2005 | Liamos et al. |
| 6,950,708 B2 | 9/2005 | Bowman, IV et al. |
| 6,958,705 B2 | 10/2005 | Lebel et al. |
| 6,959,211 B2 | 10/2005 | Rule et al. |
| 6,968,294 B2 | 11/2005 | Gutta et al. |
| 6,971,274 B2 | 12/2005 | Olin |
| 6,974,437 B2 | 12/2005 | Lebel et al. |
| 6,990,366 B2 | 1/2006 | Say et al. |
| 6,997,907 B2 | 2/2006 | Safabash et al. |
| 6,998,247 B2 | 2/2006 | Monfre et al. |
| 7,003,336 B2 | 2/2006 | Holker et al. |
| 7,003,340 B2 | 2/2006 | Say et al. |
| 7,003,341 B2 | 2/2006 | Say et al. |
| 7,024,245 B2 | 4/2006 | Lebel et al. |
| 7,025,743 B2 | 4/2006 | Mann et al. |
| 7,041,068 B2 | 5/2006 | Freeman et al. |
| 7,041,468 B2 | 5/2006 | Drucker et al. |
| 7,052,483 B2 | 5/2006 | Wojcik |
| 7,056,302 B2 | 6/2006 | Douglas |
| 7,074,307 B2 | 7/2006 | Simpson et al. |
| 7,081,195 B2 | 7/2006 | Simpson et al. |
| 7,098,803 B2 | 8/2006 | Mann et al. |
| 7,108,778 B2 | 9/2006 | Simpson et al. |
| 7,110,803 B2 | 9/2006 | Shults et al. |
| 7,113,821 B1 | 9/2006 | Sun et al. |
| 7,129,836 B2 | 10/2006 | Lawson et al. |
| 7,134,999 B2 | 11/2006 | Brauker et al. |
| 7,136,689 B2 | 11/2006 | Shults et al. |
| 7,171,274 B2 | 1/2007 | Starkweather et al. |
| 7,190,988 B2 | 3/2007 | Say et al. |
| 7,192,450 B2 | 3/2007 | Brauker et al. |
| 7,198,606 B2 | 4/2007 | Boecker et al. |
| 7,226,978 B2 | 6/2007 | Tapsak et al. |
| 7,276,029 B2 | 10/2007 | Goode, Jr. et al. |
| 7,278,983 B2 | 10/2007 | Ireland et al. |
| 7,297,151 B2 | 11/2007 | Boecker et al. |
| 7,299,081 B2 * | 11/2007 | Mace et al. .................. 600/345 |
| 7,299,082 B2 | 11/2007 | Feldman et al. |
| 7,303,726 B2 | 12/2007 | McAllister et al. |
| 7,310,544 B2 | 12/2007 | Brister et al. |
| 7,335,294 B2 | 2/2008 | Heller et al. |
| 7,340,309 B2 | 3/2008 | Miazga et al. |
| 7,364,592 B2 | 4/2008 | Carr-Brendel et al. |
| 7,366,556 B2 | 4/2008 | Brister et al. |
| 7,379,765 B2 | 5/2008 | Petisce et al. |
| 7,416,541 B2 | 8/2008 | Yuzhakov et al. |
| 7,424,318 B2 | 9/2008 | Brister et al. |
| 7,460,898 B2 | 12/2008 | Brister et al. |
| 7,467,003 B2 | 12/2008 | Brister et al. |
| 7,471,972 B2 | 12/2008 | Rhodes et al. |
| 7,494,465 B2 | 2/2009 | Brister et al. |
| 7,497,827 B2 | 3/2009 | Brister et al. |
| 7,519,408 B2 | 4/2009 | Rasdal et al. |
| 7,583,990 B2 | 9/2009 | Goode, Jr. et al. |
| 7,591,801 B2 | 9/2009 | Brauker et al. |
| 7,599,726 B2 | 10/2009 | Goode, Jr. et al. |
| 7,613,491 B2 | 11/2009 | Boock et al. |
| 7,615,007 B2 | 11/2009 | Shults et al. |
| 7,632,228 B2 | 12/2009 | Brauker et al. |
| 7,637,868 B2 | 12/2009 | Saint et al. |
| 7,640,048 B2 | 12/2009 | Dobbles et al. |
| 7,651,596 B2 | 1/2010 | Petisce et al. |
| 7,654,956 B2 | 2/2010 | Brister et al. |
| 7,657,297 B2 | 2/2010 | Simpson et al. |
| 7,666,149 B2 | 2/2010 | Simons et al. |
| 7,711,402 B2 | 5/2010 | Shults et al. |
| 7,713,574 B2 | 5/2010 | Brister et al. |
| 7,715,893 B2 | 5/2010 | Kamath et al. |
| 7,722,536 B2 | 5/2010 | Goodnow |
| 2002/0013538 A1 | 1/2002 | Teller |
| 2002/0019022 A1 | 2/2002 | Dunn et al. |
| 2002/0022855 A1 | 2/2002 | Bobroff et al. |
| 2002/0023852 A1 | 2/2002 | McIvor et al. |
| 2002/0042090 A1 | 4/2002 | Heller et al. |
| 2002/0082487 A1 | 6/2002 | Kollias et al. |
| 2002/0103499 A1 | 8/2002 | Perez et al. |
| 2002/0106709 A1 | 8/2002 | Potts et al. |
| 2002/0119711 A1 | 8/2002 | VanAntwerp et al. |
| 2002/0128594 A1 | 9/2002 | Das et al. |
| 2002/0161288 A1 | 10/2002 | Shin et al. |
| 2002/0165462 A1 | 11/2002 | Westbrook et al. |
| 2002/0198444 A1 | 12/2002 | Ughigaki et al. |
| 2003/0023317 A1 | 1/2003 | Brauker et al. |

(56) References Cited

U.S. PATENT DOCUMENTS

| | | |
|---|---|---|
| 2003/0023461 A1 | 1/2003 | Quintanilla et al. |
| 2003/0032867 A1 | 2/2003 | Crothall et al. |
| 2003/0032874 A1 | 2/2003 | Rhodes et al. |
| 2003/0042137 A1 | 3/2003 | Mao et al. |
| 2003/0065308 A1 | 4/2003 | Lebel et al. |
| 2003/0069510 A1 | 4/2003 | Semler |
| 2003/0078481 A1 | 4/2003 | McIvor et al. |
| 2003/0097092 A1 | 5/2003 | Flaherty |
| 2003/0100040 A1 | 5/2003 | Bonnecaze et al. |
| 2003/0106940 A1 | 6/2003 | Bukowski |
| 2003/0109775 A1 | 6/2003 | O'Neil et al. |
| 2003/0134347 A1 | 7/2003 | Heller et al. |
| 2003/0144581 A1 | 7/2003 | Conn et al. |
| 2003/0144608 A1 | 7/2003 | Kojima et al. |
| 2003/0168338 A1 | 9/2003 | Gao et al. |
| 2003/0176933 A1 | 9/2003 | Lebel et al. |
| 2003/0187338 A1 | 10/2003 | Say et al. |
| 2003/0199790 A1 | 10/2003 | Boecker et al. |
| 2003/0199910 A1 | 10/2003 | Boecker et al. |
| 2003/0212379 A1 | 11/2003 | Bylund et al. |
| 2003/0217966 A1 | 11/2003 | Tapsak et al. |
| 2004/0010207 A1 | 1/2004 | Flaherty et al. |
| 2004/0011671 A1 | 1/2004 | Shults et al. |
| 2004/0040840 A1 | 3/2004 | Mao et al. |
| 2004/0045879 A1 | 3/2004 | Shults et al. |
| 2004/0054263 A1 | 3/2004 | Moerman et al. |
| 2004/0064068 A1 | 4/2004 | DeNuzzio et al. |
| 2004/0106858 A1 | 6/2004 | Say et al. |
| 2004/0106859 A1 | 6/2004 | Say et al. |
| 2004/0122353 A1 | 6/2004 | Shahmirian et al. |
| 2004/0133164 A1 | 7/2004 | Funderburk et al. |
| 2004/0135684 A1 | 7/2004 | Steinthal et al. |
| 2004/0138588 A1 | 7/2004 | Saikley et al. |
| 2004/0152622 A1 | 8/2004 | Keith et al. |
| 2004/0155079 A1 | 8/2004 | Shetler et al. |
| 2004/0167801 A1 | 8/2004 | Say et al. |
| 2004/0171921 A1 | 9/2004 | Say et al. |
| 2004/0176672 A1 | 9/2004 | Silver et al. |
| 2004/0186362 A1 | 9/2004 | Brauker et al. |
| 2004/0186365 A1 | 9/2004 | Jin et al. |
| 2004/0193090 A1 | 9/2004 | Lebel et al. |
| 2004/0199059 A1 | 10/2004 | Brauker et al. |
| 2004/0204687 A1 | 10/2004 | Mogensen et al. |
| 2004/0225338 A1 | 11/2004 | Lebel et al. |
| 2004/0236200 A1 | 11/2004 | Say et al. |
| 2004/0236251 A1 | 11/2004 | Roe et al. |
| 2004/0254433 A1 | 12/2004 | Bandis et al. |
| 2004/0254434 A1 | 12/2004 | Goodnow et al. |
| 2004/0267300 A1 | 12/2004 | Mace |
| 2005/0003470 A1 | 1/2005 | Nelson et al. |
| 2005/0004494 A1 | 1/2005 | Perez et al. |
| 2005/0010269 A1 | 1/2005 | Lebel et al. |
| 2005/0027177 A1 | 2/2005 | Shin et al. |
| 2005/0031689 A1 | 2/2005 | Shults et al. |
| 2005/0043598 A1 | 2/2005 | Goode, Jr. et al. |
| 2005/0070819 A1 | 3/2005 | Poux et al. |
| 2005/0090607 A1 | 4/2005 | Tapsak et al. |
| 2005/0101875 A1 | 5/2005 | Semler et al. |
| 2005/0112169 A1 | 5/2005 | Brauker et al. |
| 2005/0114068 A1 | 5/2005 | Chey et al. |
| 2005/0121322 A1 | 6/2005 | Say et al. |
| 2005/0131346 A1 | 6/2005 | Douglas |
| 2005/0137573 A1 | 6/2005 | McLaughlin |
| 2005/0143635 A1 | 6/2005 | Kamath et al. |
| 2005/0154410 A1 | 7/2005 | Conway et al. |
| 2005/0176136 A1 | 8/2005 | Burd et al. |
| 2005/0182306 A1 | 8/2005 | Sloan |
| 2005/0187720 A1 | 8/2005 | Goode, Jr. et al. |
| 2005/0192557 A1 | 9/2005 | Brauker et al. |
| 2005/0195930 A1 | 9/2005 | Spital et al. |
| 2005/0197554 A1 | 9/2005 | Polcha |
| 2005/0199494 A1 | 9/2005 | Say et al. |
| 2005/0203360 A1 | 9/2005 | Brauker et al. |
| 2005/0222518 A1 | 10/2005 | Dib |
| 2005/0239154 A1 | 10/2005 | Feldman et al. |
| 2005/0239156 A1 | 10/2005 | Drucker et al. |
| 2005/0241957 A1 | 11/2005 | Mao et al. |
| 2005/0245795 A1 | 11/2005 | Goode, Jr. et al. |
| 2005/0245799 A1 | 11/2005 | Brauker et al. |
| 2005/0277164 A1 | 12/2005 | Drucker et al. |
| 2005/0287620 A1 | 12/2005 | Heller et al. |
| 2006/0001538 A1 | 1/2006 | Kraft et al. |
| 2006/0004303 A1 | 1/2006 | Weidenhaupt et al. |
| 2006/0010098 A1 | 1/2006 | Goodnow et al. |
| 2006/0015020 A1 | 1/2006 | Neale et al. |
| 2006/0015024 A1 | 1/2006 | Brister et al. |
| 2006/0016700 A1 | 1/2006 | Brister et al. |
| 2006/0019327 A1 | 1/2006 | Brister et al. |
| 2006/0020186 A1 | 1/2006 | Brister et al. |
| 2006/0020187 A1 | 1/2006 | Brister et al. |
| 2006/0020188 A1 | 1/2006 | Kamath et al. |
| 2006/0020189 A1 | 1/2006 | Brister et al. |
| 2006/0020190 A1 | 1/2006 | Kamath et al. |
| 2006/0020191 A1 | 1/2006 | Brister et al. |
| 2006/0020192 A1 | 1/2006 | Brister et al. |
| 2006/0036139 A1 | 2/2006 | Brister et al. |
| 2006/0036140 A1 | 2/2006 | Brister et al. |
| 2006/0036141 A1 | 2/2006 | Kamath et al. |
| 2006/0036142 A1 | 2/2006 | Brister et al. |
| 2006/0036143 A1 | 2/2006 | Brister et al. |
| 2006/0036144 A1 | 2/2006 | Brister et al. |
| 2006/0036145 A1 | 2/2006 | Brister et al. |
| 2006/0094986 A1 | 5/2006 | Neel et al. |
| 2006/0166629 A1 | 7/2006 | Reggiardo |
| 2006/0173444 A1 | 8/2006 | Choy et al. |
| 2006/0189863 A1 | 8/2006 | Heller et al. |
| 2006/0195029 A1 | 8/2006 | Shults et al. |
| 2006/0200970 A1 | 9/2006 | Brister et al. |
| 2006/0222566 A1 | 10/2006 | Brauker et al. |
| 2006/0226985 A1 | 10/2006 | Goodnow et al. |
| 2006/0247508 A1 | 11/2006 | Fennell |
| 2006/0258929 A1 | 11/2006 | Goode, Jr. et al. |
| 2007/0016381 A1 | 1/2007 | Kamath et al. |
| 2007/0027381 A1 | 2/2007 | Stafford |
| 2007/0060814 A1 | 3/2007 | Stafford |
| 2007/0073129 A1 | 3/2007 | Shah et al. |
| 2007/0078320 A1 | 4/2007 | Stafford |
| 2007/0078321 A1 | 4/2007 | Mazza et al. |
| 2007/0078322 A1 | 4/2007 | Stafford |
| 2007/0106135 A1 | 5/2007 | Sloan et al. |
| 2007/0149875 A1 | 6/2007 | Ouyang et al. |
| 2007/0163880 A1 | 7/2007 | Woo et al. |
| 2007/0173706 A1 | 7/2007 | Neinast et al. |
| 2007/0179404 A1 | 8/2007 | Escutia et al. |
| 2007/0191701 A1 | 8/2007 | Feldman et al. |
| 2007/0203407 A1 | 8/2007 | Hoss et al. |
| 2007/0203966 A1 | 8/2007 | Brauker et al. |
| 2007/0235331 A1 | 10/2007 | Simpson et al. |
| 2007/0244398 A1 | 10/2007 | Lo et al. |
| 2007/0249922 A1 | 10/2007 | Peyser et al. |
| 2008/0009692 A1 | 1/2008 | Stafford |
| 2008/0017522 A1 | 1/2008 | Heller et al. |
| 2008/0021666 A1 | 1/2008 | Goode, Jr. et al. |
| 2008/0029391 A1 | 2/2008 | Mao et al. |
| 2008/0033254 A1 | 2/2008 | Kamath et al. |
| 2008/0033268 A1 | 2/2008 | Stafford |
| 2008/0039702 A1 | 2/2008 | Hayter et al. |
| 2008/0045824 A1 | 2/2008 | Tapsak et al. |
| 2008/0060955 A1 | 3/2008 | Goodnow |
| 2008/0071156 A1 | 3/2008 | Brister et al. |
| 2008/0083617 A1 | 4/2008 | Simpson et al. |
| 2008/0086042 A1 | 4/2008 | Brister et al. |
| 2008/0086044 A1 | 4/2008 | Brister et al. |
| 2008/0086273 A1 | 4/2008 | Shults et al. |
| 2008/0097246 A1 | 4/2008 | Stafford |
| 2008/0099332 A1* | 5/2008 | Scott et al. ............... 204/403.01 |
| 2008/0108942 A1 | 5/2008 | Brister et al. |
| 2008/0114280 A1 | 5/2008 | Stafford |
| 2008/0119707 A1 | 5/2008 | Stafford |
| 2008/0183061 A1 | 7/2008 | Goode, Jr. et al. |
| 2008/0183399 A1 | 7/2008 | Goode, Jr. et al. |
| 2008/0188731 A1 | 8/2008 | Brister et al. |
| 2008/0189051 A1 | 8/2008 | Goode, Jr. et al. |
| 2008/0194935 A1 | 8/2008 | Brister et al. |

(56) References Cited

U.S. PATENT DOCUMENTS

| | | |
|---|---|---|
| 2008/0194936 A1 | 8/2008 | Goode, Jr. et al. |
| 2008/0194937 A1 | 8/2008 | Goode, Jr. et al. |
| 2008/0194938 A1 | 8/2008 | Brister et al. |
| 2008/0195232 A1 | 8/2008 | Carr-Brendel et al. |
| 2008/0195967 A1 | 8/2008 | Goode, Jr. et al. |
| 2008/0197024 A1 | 8/2008 | Simpson et al. |
| 2008/0200788 A1 | 8/2008 | Brister et al. |
| 2008/0200789 A1 | 8/2008 | Brister et al. |
| 2008/0200791 A1 | 8/2008 | Simpson et al. |
| 2008/0200897 A1 | 8/2008 | Hoss et al. |
| 2008/0208025 A1 | 8/2008 | Shults et al. |
| 2008/0214915 A1 | 9/2008 | Brister et al. |
| 2008/0214918 A1 | 9/2008 | Brister et al. |
| 2008/0228051 A1 | 9/2008 | Shults et al. |
| 2008/0228054 A1 | 9/2008 | Shults et al. |
| 2008/0242961 A1 | 10/2008 | Brister et al. |
| 2008/0262469 A1 | 10/2008 | Brister et al. |
| 2008/0275313 A1 | 11/2008 | Brister et al. |
| 2008/0287764 A1 | 11/2008 | Rasdal et al. |
| 2008/0287765 A1 | 11/2008 | Rasdal et al. |
| 2008/0287766 A1 | 11/2008 | Rasdal et al. |
| 2008/0296155 A1 | 12/2008 | Shults et al. |
| 2008/0300476 A1 | 12/2008 | Stafford |
| 2008/0306368 A1 | 12/2008 | Goode, Jr. et al. |
| 2008/0306434 A1 | 12/2008 | Dobbles et al. |
| 2008/0306435 A1 | 12/2008 | Kamath et al. |
| 2008/0306444 A1 | 12/2008 | Brister et al. |
| 2009/0012379 A1 | 1/2009 | Goode, Jr. et al. |
| 2009/0018424 A1 | 1/2009 | Kamath et al. |
| 2009/0030294 A1 | 1/2009 | Petisce et al. |
| 2009/0036758 A1 | 2/2009 | Brauker et al. |
| 2009/0036763 A1 | 2/2009 | Brauker et al. |
| 2009/0043181 A1 | 2/2009 | Brauker et al. |
| 2009/0043182 A1 | 2/2009 | Brauker et al. |
| 2009/0043525 A1 | 2/2009 | Brauker et al. |
| 2009/0043541 A1 | 2/2009 | Brauker et al. |
| 2009/0043542 A1 | 2/2009 | Brauker et al. |
| 2009/0045055 A1 | 2/2009 | Rhodes et al. |
| 2009/0048501 A1 | 2/2009 | Goodnow et al. |
| 2009/0062633 A1 | 3/2009 | Brauker et al. |
| 2009/0062635 A1 | 3/2009 | Brauker et al. |
| 2009/0076356 A1 | 3/2009 | Simpson et al. |
| 2009/0076359 A1 | 3/2009 | Peyser |
| 2009/0076360 A1 | 3/2009 | Brister et al. |
| 2009/0076361 A1 | 3/2009 | Kamath et al. |
| 2009/0082693 A1 | 3/2009 | Stafford |
| 2009/0099436 A1 | 4/2009 | Brister et al. |
| 2009/0102678 A1 | 4/2009 | Stafford et al. |
| 2009/0105569 A1 | 4/2009 | Stafford |
| 2009/0124877 A1 | 5/2009 | Goode et al. |
| 2009/0124878 A1 | 5/2009 | Goode et al. |
| 2009/0124879 A1 | 5/2009 | Brister et al. |
| 2009/0124964 A1 | 5/2009 | Leach et al. |
| 2009/0131768 A1 | 5/2009 | Simpson et al. |
| 2009/0131769 A1 | 5/2009 | Leach et al. |
| 2009/0131776 A1 | 5/2009 | Simpson et al. |
| 2009/0131777 A1 | 5/2009 | Simpson et al. |
| 2009/0137886 A1 | 5/2009 | Shariati et al. |
| 2009/0137887 A1 | 5/2009 | Shariati et al. |
| 2009/0143659 A1 | 6/2009 | Li et al. |
| 2009/0143660 A1 | 6/2009 | Brister et al. |
| 2009/0156919 A1 | 6/2009 | Brister et al. |
| 2009/0156924 A1 | 6/2009 | Shariati et al. |
| 2009/0163790 A1 | 6/2009 | Brister et al. |
| 2009/0163791 A1 | 6/2009 | Brister et al. |
| 2009/0171182 A1 | 7/2009 | Stafford |
| 2009/0178459 A1 | 7/2009 | Li et al. |
| 2009/0182217 A1 | 7/2009 | Li et al. |
| 2009/0192366 A1 | 7/2009 | Mensinger et al. |
| 2009/0192380 A1 | 7/2009 | Shariati et al. |
| 2009/0192722 A1 | 7/2009 | Shariati et al. |
| 2009/0192724 A1 | 7/2009 | Brauker et al. |
| 2009/0192745 A1 | 7/2009 | Kamath et al. |
| 2009/0192751 A1 | 7/2009 | Kamath et al. |
| 2009/0203981 A1 | 8/2009 | Brauker et al. |
| 2009/0204341 A1 | 8/2009 | Brauker et al. |
| 2009/0216103 A1 | 8/2009 | Brister et al. |
| 2009/0240120 A1 | 9/2009 | Mensinger et al. |
| 2009/0240128 A1 | 9/2009 | Mensinger et al. |
| 2009/0240193 A1 | 9/2009 | Mensinger et al. |
| 2009/0242399 A1 | 10/2009 | Kamath et al. |
| 2009/0242425 A1 | 10/2009 | Kamath et al. |
| 2009/0247855 A1 | 10/2009 | Boock et al. |
| 2009/0247856 A1 | 10/2009 | Boock et al. |
| 2009/0287073 A1 | 11/2009 | Boock et al. |
| 2009/0287074 A1 | 11/2009 | Shults et al. |
| 2009/0299155 A1 | 12/2009 | Yang et al. |
| 2009/0299156 A1 | 12/2009 | Simpson et al. |
| 2009/0299162 A1 | 12/2009 | Brauker et al. |
| 2009/0299276 A1 | 12/2009 | Brauker et al. |
| 2010/0010324 A1 | 1/2010 | Brauker et al. |
| 2010/0010331 A1 | 1/2010 | Brauker et al. |
| 2010/0010332 A1 | 1/2010 | Brauker et al. |
| 2010/0016687 A1 | 1/2010 | Brauker et al. |
| 2010/0016698 A1 | 1/2010 | Rasdal et al. |
| 2010/0022855 A1 | 1/2010 | Brauker et al. |
| 2010/0030038 A1 | 2/2010 | Brauker et al. |
| 2010/0030053 A1 | 2/2010 | Goode, Jr. et al. |
| 2010/0030484 A1 | 2/2010 | Brauker et al. |
| 2010/0030485 A1 | 2/2010 | Brauker et al. |
| 2010/0036215 A1 | 2/2010 | Goode, Jr. et al. |
| 2010/0036216 A1 | 2/2010 | Goode, Jr. et al. |
| 2010/0036222 A1 | 2/2010 | Goode, Jr. et al. |
| 2010/0036223 A1 | 2/2010 | Goode, Jr. et al. |
| 2010/0036225 A1 | 2/2010 | Goode, Jr. et al. |
| 2010/0041971 A1 | 2/2010 | Goode, Jr. et al. |
| 2010/0045465 A1 | 2/2010 | Brauker et al. |
| 2010/0049024 A1 | 2/2010 | Saint et al. |
| 2010/0052293 A1 | 3/2010 | Brooks et al. |
| 2010/0063373 A1 | 3/2010 | Kamath et al. |
| 2010/0076283 A1 | 3/2010 | Simpson et al. |
| 2010/0076290 A1 | 3/2010 | Bernstein et al. |
| 2010/0081908 A1 | 4/2010 | Dobbles et al. |
| 2010/0081910 A1 | 4/2010 | Brister et al. |
| 2010/0087724 A1 | 4/2010 | Brauker et al. |
| 2010/0096259 A1 | 4/2010 | Zhang et al. |
| 2010/0099970 A1 | 4/2010 | Shults et al. |
| 2010/0099971 A1 | 4/2010 | Shults et al. |
| 2010/0119693 A1 | 5/2010 | Tapsak et al. |
| 2010/0121169 A1 | 5/2010 | Petisce et al. |

FOREIGN PATENT DOCUMENTS

| | | |
|---|---|---|
| EP | 0127958 | 12/1984 |
| EP | 0320109 | 6/1989 |
| EP | 0353328 | 2/1990 |
| EP | 0390390 | 10/1990 |
| EP | 0396788 | 11/1990 |
| EP | 0286118 | 1/1995 |
| EP | 1048264 | 11/2000 |
| EP | 1177802 | 2/2002 |
| EP | 2060284 | 5/2009 |
| WO | WO-96/25089 | 8/1996 |
| WO | WO-96/35370 | 11/1996 |
| WO | WO-98/35053 | 8/1998 |
| WO | WO-99/56613 | 11/1999 |
| WO | WO-00/49940 | 8/2000 |
| WO | WO-00/59370 | 10/2000 |
| WO | WO-00/78992 | 12/2000 |
| WO | WO-01/52935 | 7/2001 |
| WO | WO-01/54753 | 8/2001 |
| WO | WO-02/16905 | 2/2002 |
| WO | WO-02/058537 | 8/2002 |
| WO | WO-03/076893 | 9/2003 |
| WO | WO-03/082091 | 10/2003 |
| WO | WO-2004/061420 | 7/2004 |
| WO | WO-2005/089103 | 9/2005 |
| WO | WO-2007/016399 | 2/2007 |
| WO | WO-2007/027788 | 3/2007 |
| WO | WO-2007/041069 | 4/2007 |
| WO | WO-2007/041070 | 4/2007 |
| WO | WO-2007/041248 | 4/2007 |
| WO | WO-2007/120363 | 10/2007 |
| WO | WO-2007/143225 | 12/2007 |

(56) References Cited

FOREIGN PATENT DOCUMENTS

| WO | WO-2008/031106 | 3/2008 |
|----|---|---|
| WO | WO-2008/031110 | 3/2008 |
| WO | WO-2008/039944 | 4/2008 |
| WO | WO-2008/051920 | 5/2008 |
| WO | WO-2008/051924 | 5/2008 |
| WO | WO-2008/103620 | 8/2008 |
| WO | WO-2008/150917 | 12/2008 |
| WO | WO-2009/062675 | 5/2009 |

OTHER PUBLICATIONS

Armour, J. C., et al., "Application of Chronic Intravascular Blood Glucose Sensor in Dogs", *Diabetes*, vol. 39, 1990, pp. 1519-1526.

Aussedat, B., et al., "A User-Friendly Method for Calibrating a Subcutaneous Glucose Sensor-Based Hypoglycaemic Alarm", *Biosensors & Bioelectronics*, vol. 12, No. 11, 1997, pp. 1061-1071.

Bennion, N., et al., "Alternate Site Glucose Testing: A Crossover Design", *Diabetes Technology & Therapeutics*, vol. 4, No. 1, 2002, pp. 25-33.

Blank, T. B., et al., "Clinical Results From a Non-Invasive Blood Glucose Monitor", *Optical Diagnostics and Sensing of Biological Fluids and Glucose and Cholesterol Monitoring II, Proceedings of SPIE*, vol. 4624, 2002, pp. 1-10.

Brooks, S. L., et al., "Development of an On-Line Glucose Sensor for Fermentation Monitoring", *Biosensors*, vol. 3, 1987/88, pp. 45-56.

Cass, A. E., et al., "Ferrocene-Medicated Enzyme Electrode for Amperometric Determination of Glucose", *Analytical Chemistry*, vol. 56, No. 4, 1984, 667-671.

Csoregi, E., et al., "Design and Optimization of a Selective Subcutaneously Implantable Glucose Electrode Based on 'Wired' Glucose Oxidase", *Analytical Chemistry*, vol. 67, No. 7, 1995, pp. 1240-1244.

Feldman, B., et al., "A Continuous Glucose Sensor Based on Wired Enzyme™ Technology—Results from a 3-Day Trial in Patients with Type 1 Diabetes", *Diabetes Technology & Therapeutics*, vol. 5, No. 5, 2003, pp. 769-779.

Feldman, B., et al., "Correlation of Glucose Concentrations in Interstitial Fluid and Venous Blood During Periods of Rapid Glucose Change", *Abbott Diabetes Care, Inc. Freestyle Navigator Continuous Glucose Monitor Pamphlet*, 2004.

Johnson, P. C., "Peripheral Circulation", *John Wiley & Sons*, 1978, pp. 198.

Jungheim, K., et al., "How Rapid Does Glucose Concentration Change in Daily Life of Patients with Type 1 Diabetes?", 2002, pp. 250.

Jungheim, K., et al., "Risky Delay of Hypoglycemia Detection by Glucose Monitoring at the Arm", *Diabetes Care*, vol. 24, No. 7, 2001, pp. 1303-1304.

Kaplan, S. M., "Wiley Electrical and Electronics Engineering Dictionary", *IEEE Press*, 2004, pp. 141, 142, 548, 549.

Lortz, J., et al., "What is Bluetooth? We Explain the Newest Short-Range Connectivity Technology", *Smart Computing Learning Series, Wireless Computing*, vol. 8, Issue 5, 2002, pp. 72-74.

Malin, S. F., et al., "Noninvasive Prediction of Glucose by Near-Infrared Diffuse Reflectance Spectoscopy", *Clinical Chemistry*, vol. 45, No. 9, 1999, pp. 1651-1658.

McGarraugh, G., et al., "Glucose Measurements Using Blood Extracted from the Forearm and the Finger", *TheraSense, Inc.*, 2001, 16 Pages.

McGarraugh, G., et al., "Physiological Influences on Off-Finger Glucose Testing", *Diabetes Technology & Therapeutics*, vol. 3, No. 3, 2001, pp. 367-376.

McKean, B. D., et al., "A Telemetry-Instrumentation System for Chronically Implanted Glucose and Oxygen Sensors", *IEEE Transactions on Biomedical Engineering*, vol. 35, No. 7, 1988, pp. 526-532.

Pickup, J., et al., "Implantable Glucose Sensors: Choosing the Appropriate Sensing Strategy", *Biosensors*, vol. 3, 1987/88, pp. 335-346.

Pickup, J., et al., "In Vivo Molecular Sensing in Diabetes Mellitus: An Implantable Glucose Sensor with Direct Electron Transfer", *Diabetologia*, vol. 32, 1989, pp. 213-217.

Pishko, M. V., et al., "Amperometric Glucose Microelectrodes Prepared Through Immobilization of Glucose Oxidase in Redox Hydrogels", *Analytical Chemistry*, vol. 63, No. 20, 1991, pp. 2268-2272.

Quinn, C. P., et al., "Kinetics of Glucose Delivery to Subcutaneous Tissue in Rats Measured with 0.3-mm Amperometric Microsensors", *The American Physiological Society*, 1995, E155-E161.

Roe, J. N., et al., "Bloodless Glucose Measurements", *Critical Review in Therapeutic Drug Carrier Systems*, vol. 15, Issue 3, 1998, pp. 199-241.

Sakakida, M., et al., "Development of Ferrocene-Mediated Needle-Type Glucose Sensor as a Measure of True Subcutaneous Tissue Glucose Concentrations", *Artificial Organs Today*, vol. 2, No. 2, 1992, pp. 145-158.

Sakakida, M., et al., "Ferrocene-Mediated Needle-Type Glucose Sensor Covered with Newly Designed Biocompatible Membrane", *Sensors and Actuators B*, vol. 13-14, 1993, pp. 319-322.

Salehi, C., et al., "A Telemetry-Instrumentation System for Long-Term Implantable Glucose and Oxygen Sensors", *Analytical Letters*, vol. 29, No. 13, 1996, pp. 2289-2308.

Schmidt, F. J., et al., "Calibration of a Wearable Glucose Sensor", *The International Journal of Artificial Organs*, vol. 15, No. 1, 1992, pp. 55-61.

Schmidtke, D. W., et al., "Measurement and Modeling of the Transient Difference Between Blood and Subcutaneous Glucose Concentrations in the Rat After Injection of Insulin", *Proceedings of the National Academy of Sciences*, vol. 95, 1998, pp. 294-299.

Shaw, G. W., et al., "In Vitro Testing of a Simply Constructed, Highly Stable Glucose Sensor Suitable for Implantation in Diabetic Patients", *Biosensors & Bioelectronics*, vol. 6, 1991, pp. 401-406.

Shichiri, M., et al., "Glycaemic Control in Pancreatectomized Dogs with a Wearable Artificial Endocrine Pancreas", *Diabetologia*, vol. 24, 1983, pp. 179-184.

Shichiri, M., et al., "In Vivo Characteristics of Needle-Type Glucose Sensor—Measurements of Subcutaneous Glucose Concentrations in Human Volunteers", *Hormone and Metabolic Research Supplement Series*, vol. 20, 1988, pp. 17-20.

Shichiri, M., et al., "Membrane Design for Extending the Long-Life of an Implantable Glucose Sensor", *Diabetes Nutrition and Metabolism*, vol. 2, 1989, pp. 309-313.

Shichiri, M., et al., "Needle-type Glucose Sensor for Wearable Artificial Endocrine Pancreas", *Implantable Sensors for Closed-Loop Prosthetic Systems*, Chapter 15, 1985, pp. 197-210.

Shichiri, M., et al., "Telemetry Glucose Monitoring Device With Needle-Type Glucose Sensor: A Useful Tool for Blood Glucose Monitoring in Diabetic Individuals", *Diabetes Care*, vol. 9, No. 3, 1986, pp. 298-301.

Shichiri, M., et al., "Wearable Artificial Endocrine Pancreas With Needle-Type Glucose Sensor", *The Lancet*, 1982, pp. 1129-1131.

Shults, M. C., et al., "A Telemetry-Instrumentation System for Monitoring Multiple Subcutaneously Implanted Glucose Sensors", *IEEE Transactions on Biomedical Engineering*, vol. 41, No. 10, 1994, pp. 937-942.

Sternberg, R., et al., "Study and Development of Multilayer Needle-Type Enzyme-Based Glucose Microsensors", *Biosensors*, vol. 4, 1988, pp. 27-40.

Thompson, M., et al., "In Vivo Probes: Problems and Perspectives", *Clinical Biochemistry*, vol. 19, 1986, pp. 255-261.

Turner, A., et al., "Diabetes Mellitus: Biosensors for Research and Management", *Biosensors*, vol. 1, 1985, pp. 85-115.

Updike, S. J., et al., "Principles of Long-Term Fully Implanted Sensors with Emphasis on Radiotelemetric Monitoring of Blood Glucose from Inside a Subcutaneous Foreign Body Capsule (FBC)", *Biosensors in the Body: Continuous in vivo Monitoring*, Chapter 4, 1997, pp. 117-137.

Velho, G., et al., "Strategies for Calibrating a Subcutaneous Glucose Sensor", *Biomedica Biochimica Acta*, vol. 48, 1989, pp. 957-964.

*Wiley Electrical and Electronics Engineering Dictionary*, John Wiley & Sons, Inc., 2004, pp. 141, 142, 548, 549.

Wilson, G. S., et al., "Progress Toward the Development of an Implantable Sensor for Glucose", *Clinical Chemistry*, vol. 38, No. 9, 1992, pp. 1613-1617.

\* cited by examiner

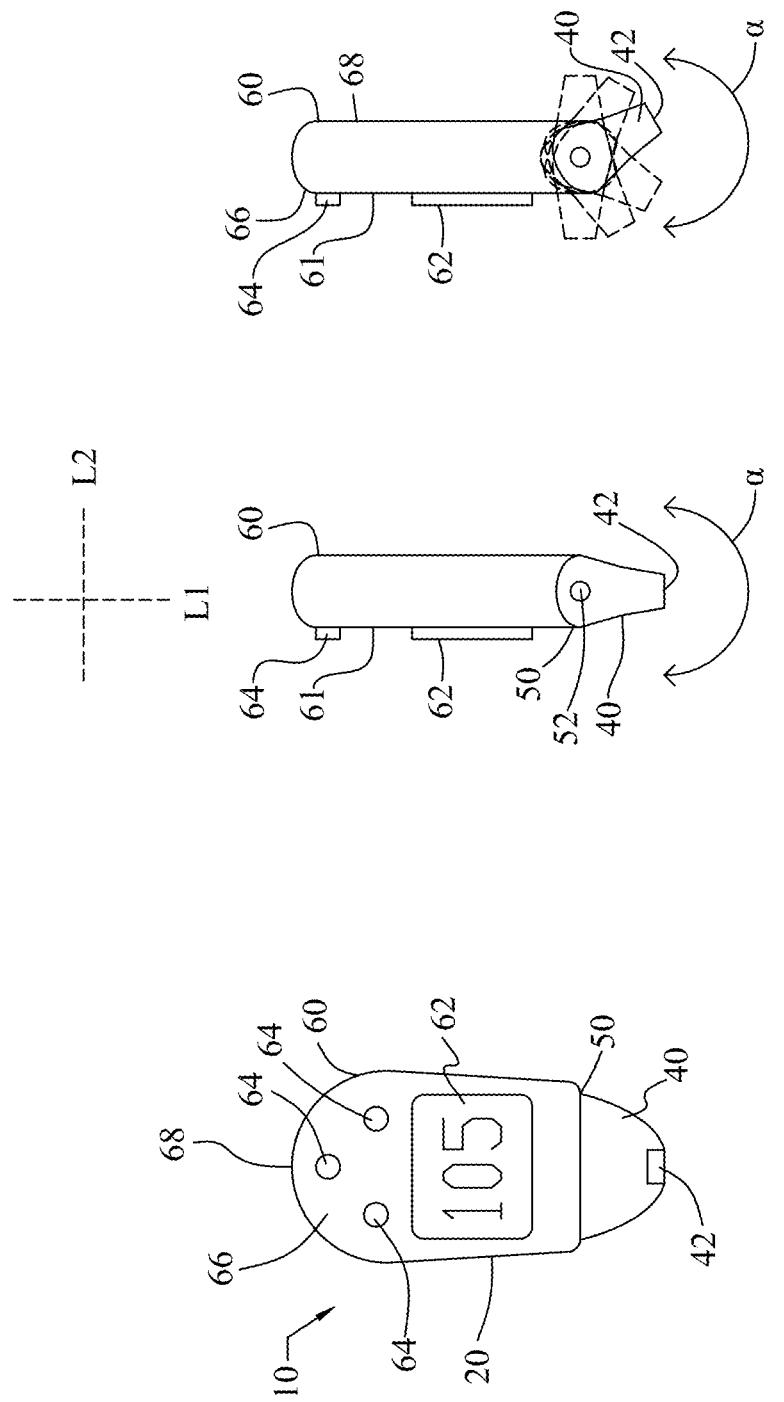

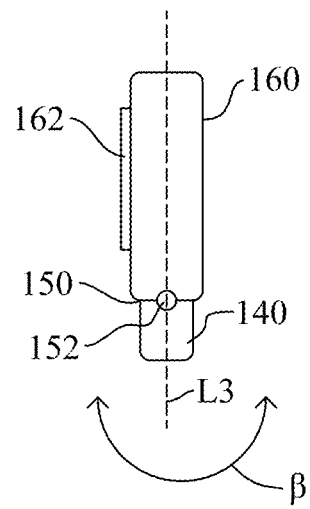
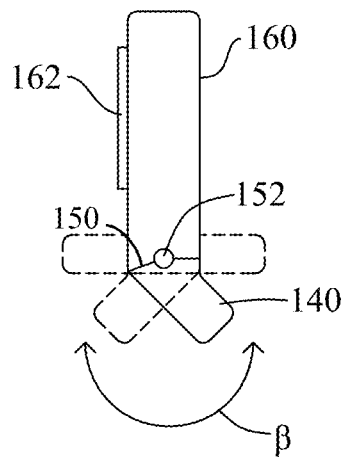
FIG. 6     FIG. 7
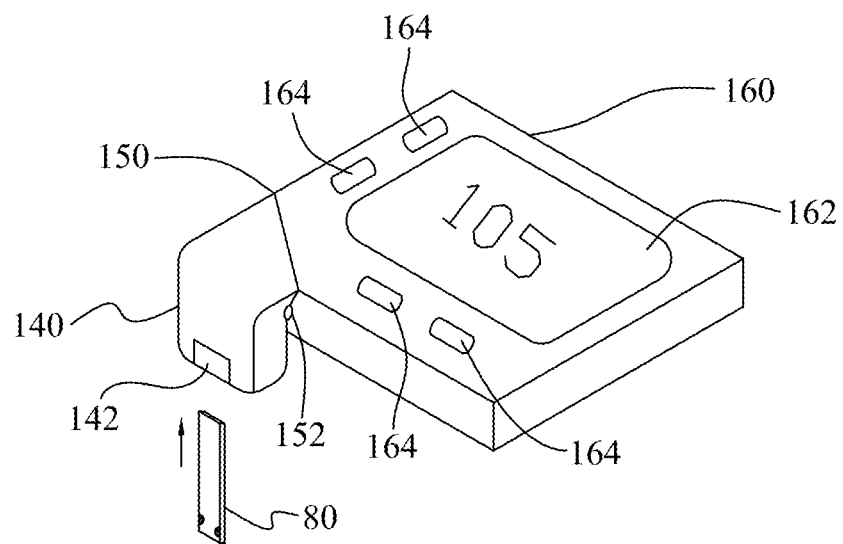
FIG. 8

ANALYTE METER WITH A MOVEABLE HEAD AND METHODS OF USING THE SAME

BACKGROUND

Analytical analyte testers and meters are often used in chemistry and medicine to determine the presence and/or concentration of a biological analyte of interest. For example, such analytical testers and meters are used to monitor glucose in diabetic patients and lactate during critical care events.

Many currently available analyte meters are configured such that an in vitro analyte tester, oftentimes in the form of a test strip, is inserted into the analyte meter for the testing process. Such meters include in vitro analyte test strip ports to receive analyte sensors for testing. Conventional analyte meters have in vitro analyte test strip ports that have fixed arrangements, i.e., sensor ports in fixed or immovable positions relative to the rest of the meter. Because of this, after obtaining a sample of biological fluid for analyte testing, a user may have to change the orientation of the meter in order to view analyte test results that are displayed on a display of the meter. This fixed orientation of the sensor port relative to other portions of a meter may complicate and make difficult the testing process. For example, users of an analyte meter may have physical ailments, e.g., as a result of a health condition, that make testing using a fixed-oriented meter challenging. In the context of diabetes care, manual dexterity, vision, and the like may be compromised. These and other problems may be compounded when a user is very young or very old.

It would therefore be desirable and useful to develop analyte meters, e.g., glucose testing meters, that are easy to use and do not require a user to change the orientation of the meter in order to obtain test results.

SUMMARY

The present disclosure provides devices and methods for analyte testing. Embodiments include analyte meters having adjustable in vitro analyte test strip contacting areas that can be adjusted to a particular test site. Included herein are analyte meters having moveable in vitro analyte test strip ports relative to at least a portion of a meter. The meters and methods therefore are designed to detect and/or quantify analyte levels in a fluid sample. The meters may be characterized as in vitro meters in that they test for analyte in a sample withdrawn from a user and applied to an in vitro analyte test strip that is not implanted in the user. In other words, the meters are for ex-vivo analyte testing. As described below, the in vitro meters may be combined with in vivo analyte testing systems to provide an integrated system.

Embodiments include analyte meters, e.g., glucose meters that include programming to test glucose in a biological sample, having a housing that includes a first portion and at least a second portion coupled to the first portion by a connector portion. The first meter portion includes an in vitro analyte test strip engaging area, e.g., an in vitro analyte test strip port, to receive or otherwise make contact with (electrical and/or mechanical) an in vitro analyte testing device such as in the form of an in vitro analyte test strip. In further describing the invention, description will be primarily related to an analyte tester in the form of a test strip for exemplary purposes only, where such description is in no way intended to limit the scope of the invention. It is to be understood that an in vitro analyte tester may be in a variety of forms. The second meter portion may include other features and componentry of the meter, e.g., one or more controller modules, e.g., hardware and/or software, to accomplish testing of an analyte applied to a sample contacted to an in vitro analyte test strip. In certain embodiments, the second meter portion includes a reporting module to report results of an analyte test to a user, e.g., a visual display and/or an audio output module. In certain embodiments, the first meter portion is moveable relative to the second meter portion, or vice versa. The first meter portion may be moved so as not to cause movement of the second portion, and vice versa. Each of the first and second meter portions may move independently of one or more other portions of the meter. In certain embodiments, the first meter portion flexes, pivots, rotates, rolls, or otherwise moves relative to the second meter portion.

Embodiments include first meter portions that are pivotable about a pivot point relative to the second meter portion that includes a reporting module. First meter portions are moveable upwardly and/or downwardly relative to the second meter portion, and which may be lockable against upward or downward movement. For example, a first meter portion may be pivotable towards and/or away from the second meter portion, and thereafter, in one aspect, locked in the pivoted position.

In certain embodiments, a first meter portion can be caused to pitch and/or yaw and/or roll, where pitch, yaw and roll will be defined broadly herein with respect to rotations about axes x, y and z, including but not limited to rotation about the z-axis (pitch), rotation about the y-axis (yaw) and rotation about the x-axis (roll). In certain embodiments, the first portion may be caused to pitch and/or roll and/or yaw, while the second portion remains in a fixed position.

The devices may include locking mechanisms to lock a first meter portion in place in a selected position relative to at least a second meter portion. In certain aspects, selecting a desired position may include selecting a desired position from a plurality of possible selectable positions.

Embodiments include blood glucose meters dimensioned and designed for home use, e.g., and are compact, handholdable, and easily transportable devices. In certain embodiments, the blood glucose meters may be part of, e.g., integrated with, an in vivo analyte testing system.

These and other objects, features and advantages of the present disclosure will become more fully apparent from the following detailed description of the embodiments, the appended claims and the accompanying drawings.

BRIEF DESCRIPTION OF THE DRAWINGS

Referring now to the drawings, wherein like reference numerals and letters indicate corresponding structure throughout the several views:

FIG. 1 shows a frontal view of an embodiment of an adjustable in vitro analyte meter according to the present disclosure having an in vitro analyte test strip contacting portion that is moveable relative to at least one other portion of the meter such as a reporting module portion;

FIG. 2 shows a side view of the analyte meter of FIG. 1;

FIG. 3 shows a side view of the analyte meter of FIG. 1 with the in vitro analyte test strip head moveable about the meter connector through a range of motion (from about 0 to about 180 degrees);

FIG. 6 shows a side view of the integrated analyte meter of FIG. 5;

FIG. 7 shows a side view of the integrated analyte meter of FIG. 5 with the in vitro analyte test strip head moveable about the meter connector through a range of motion (from about 0 to about 180 degrees); and FIG. 8 shows a perspective view of the analyte meter of FIG. 5.

Figure 4:
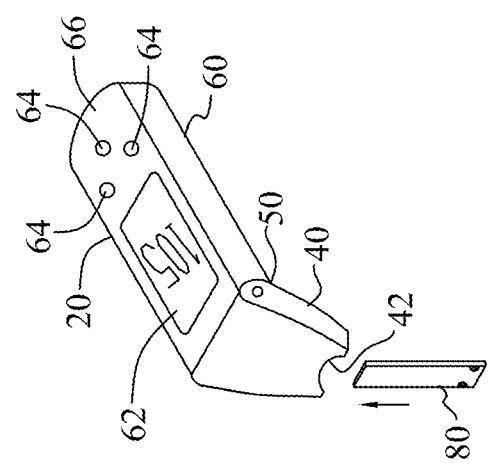
FIG. 4 shows a perspective view of the analyte meter of FIG. 1.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

DETAILED DESCRIPTION

Before the embodiments of the present disclosure are further described, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

As used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The publications discussed herein are provided solely for their disclosure prior to the filing date of the present application. Nothing herein is to be construed as an admission that the present disclosure is not entitled to antedate such publication by virtue of prior invention. Further, the dates of publication provided may be different from the actual publication dates which may need to be independently confirmed.

The present disclosure provides in vitro analyte meters designed to contact, e.g., receive, in vitro analyte test strips. The in vitro analyte meters (also referred to as single point monitors, single point blood glucose modules, blood glucose monitors or meters, and the like) are configured to process a signal received from the in vitro analyte test strip and determine a presence and/or concentration of analyte in a sample of biological fluid applied to the in vitro analyte test strip, based on the received signal. Embodiments of the in vitro meters include portions that contact in vitro analyte test strips, e.g., in vitro analyte test strip ports.

The in vitro analyte meters may be small portable devices designed and dimensioned to be palm-sized and/or adapted to fit into, for example, a pocket or purse of a patient, or comfortably worn on a belt, e.g., in a holster. The analyte meters may have the functionality and/or appearance of a personal electronic device, such as a mobile phone or personal digital assistant (PDA), so that the user may not be identified as a person using a medical device. See, e.g., U.S. Pat. Nos. 7,041, 468; 6,071,391; 6,120,676; 6,143,164; 6,299,757; 6,338,790; 6,377,894; 6,600,997; 6,773,671; 6,377,894; 6,600,997; 6,773,671; 6,514,460; 6,893,545; 6,924,518, and patent application Ser. No. 12/431,672, and Patent Application Publication No. US2004/0254434, the disclosures of each of which are herein incorporated by reference. In certain embodiments, the analyte meters may be a larger unit for home use and designed to sit on a shelf or nightstand. In yet other embodiments, the analyte meters may be designed for use in a hospital or doctor's office.

The in vitro meters include a portion that is moveable, e.g., rotatable, relative to at least one other portion of the meter while maintaining the at least one other portion in a fixed position, and in many embodiments the moveable portion is moveable relative to the entirety of the rest of the meter. It will be understood that the in vitro meters described herein are described primarily with respect to in vitro analyte test strip contacting portions of the meter being moveable relative to at least one other portion of the meter for exemplary purposes only, and the at least one other portion of the meter, including the entirety of the meter, may be moved relative to the in vitro analyte test strip contacting portion while maintaining the in vitro analyte test strip contacting portion in a fixed position.

The movable in vitro analyte test strip contacting portion may move in a variety of positions. For example, the meters may include a reporting module interface area, where reporting module is used broadly to include one or more units or components that convey information to a user of the device. By way of example and as described herein, a reporting module may include a visual display integrated with the meter housing. Embodiments include in vitro test strip-contacting meter portions that are pivoted through an angle of at least 180 degrees relative to meter or the reporting module portion of the meter (see, e.g., FIGS. 2-4), e.g., about the longitudinal and/or latitudinal meter axis(es) as shown by the dotted lines L1/L2 in FIG. 2. For example, a first meter portion pivoting motion may be characterized as upward and downward motion relative to the housing (e.g., relative to the reporting module portion of the housing) or relative to a connector portion that connects the in vitro analyte test strip contacting portion to another portion of the housing and enables it to move, and may also be referred to as frontward and backward motion as related to a surface of the meter that includes one or more user interface components such as a reporting module and/or user function selectors such that frontward movement refers to moving the in vitro analyte test strip contacting portion of a meter towards such a surface and backward movement refers to moving the in vitro analyte test strip contacting portion of a meter away from such a surface. In addition to or instead of upwardly and downwardly movement, an in vitro analyte test strip contacting portion may be moved sidewardly in one or both sideward directions. The in vitro analyte test strip contacting portion or head of the in vitro meter is therefore rotatable about its longitudinal axis and/or latitudinal axis. As to upward and downward movements, in certain embodiments an in vitro analyte test strip contacting portion may be limited in downward movement, but unlimited in upward movement, and vice versa. In certain embodiments, the in vitro analyte test strip contacting portion can rotate about one or more of its axes so as to pitch and/or yaw and/or roll. In certain embodiments, an in vitro meter may have limited pitch and/or roll, and unlimited yaw angle, or any combination thereof. Accordingly, the moveable in vitro analyte test strip contacting portion may have multiple degrees of freedom.

Referring now to the Figures, FIG. 1 shows an embodiment of an in vitro analyte meter 10 having a moveable head 40. Meter 10 includes a housing 20 having a first portion or in vitro analyte test strip contacting portion 40 (the head), and at least one other portion 60, coupled together by connector 50. First portion or meter head 40 includes an in vitro analyte test strip contacting area 42 to establish contact (electrical and/or mechanical) with an in vitro analyte test strip.

In vitro analyte test strip contacting area 42 of meter 10 may be on or in the housing, herein shown as an in vitro analyte test strip port coupled to housing 20, wherein in vitro analyte test strip port 42 is configured to receive an in vitro analyte test strip 80 as shown in FIG. 4 (see also FIG. 8). In vitro analyte test strip contacting area 42 may include one or more conductive contacts to contact conductive contacts of an analyte in vitro analyte test strip contacted therewith to establish electrical contact, in the instances of electrochemical in vitro analyte test strips. In certain embodiments, meter 10 includes optional turn-on contact(s) so that the meter 10 is activated ("turned on") to perform in vitro testing by contacting the conductive contact(s) of an in vitro test strip upon application (e.g., insertion) of an in vitro analyte test strip to the in vitro analyte test strip contact area.

Referring back to FIG. 1, second meter portion 60 may include a frontal or user interface side or wall 66 that includes one or more user interface components and an opposing side 68. As can be seen, the second meter portion 60 includes optional reporting module 62 to convey information to a user and/or enable a user and/or vice versa, e.g., to report results of an analyte test to a user. Reporting module 62 may be an audible, tactile, and/or visual reporting module, e.g., may include a display to present information such as analyte concentration, may be configured to vibrate and/or otherwise convey information to the user associated with the analyte concentration based on a series of vibratory alerts, and/or may be configured to include audible notification (e.g., may include speakers, etc.) and/or may include a voice user interface. In certain embodiments, meter 10 includes an optional display unit 62 or a port (not shown) for coupling an optional display unit to the meter 10. One or more user function selectors 64 may also be included. The manually actuatable selector(s) are arranged for convenient actuation by a user.

User function selector(s) 64 may include one or more buttons (as shown for example in the figures), knobs, jog wheel, capacitive sensing slider inputs, and/or one or more combinations thereof. In one embodiment, a user may operate one or more user function selector to navigate menus and options of reporting module 62 and to select therefrom, and may also operate input(s) to perform calculations and determinations associated with one or more medication dose calculation functions, such as a bolus dose calculation function, of the meter 10, including confirming a dose calculation prior to delivery. In a further embodiment, the one or more user function selectors may be operated to enter event marker information to the meter 10 such as, for example, meal events, exercise events and the like.

In one embodiment, user function selector 64 includes a plurality of input buttons, wherein each input button is designated for a specific task. Alternatively, one or more of the input buttons may be "soft buttons" which may be programmable or programmed in the meter 10 and selectively displayed on the display unit 62. In the case where one or more of the plurality of input buttons are "soft buttons", these buttons may be used for a variety of functions. The variety of functions may be determined based on the operational mode of the meter 10, and may be distinguishable to a user by the use of button instructions shown on display unit 62.

Reporting module in the form of a visual display 62 may be a dot-matrix display. In some embodiments, other display types, such as liquid-crystal displays (LCD), plasma displays, high definition displays (HD), light-emitting diode (LED) displays, OLED (Organic Light Emitting Device) display, seven-segment displays, color or monochrome displays, among others, may alternatively be used. A single unit may include a plurality of different displays. Display unit 62 may be configured to provide an alphanumeric display, a graphical display, a video display, an audio display, a vibratory output, or one or more combinations thereof. The display unit 62 can also be configured to provide, for example, information related to a patient's current analyte concentration as well as predictive analyte concentrations, such as trending information, and/or prior monitored analyte concentrations (for example, by a chart or a graph, numeric display over a predetermined time period).

In some embodiments, display unit 62 is a touch sensitive display in which information or commands may be entered via the display using, for example, a stylus or any other suitable input device, and where the touch sensitive display may be configured as the user interface in an icon driven environment, for example.

Referring again to FIG. 1, in certain embodiments, connector 50 couples first meter portion 40 to second meter portion 60 and enables them to selectively move independently of each other. Connector 50 may be any suitable mechanism that enables movement of first portion 40 relative to second portion 60. Connector 50 may include ball and socket, articulating joint, universal joint, rotary joint, pawl/ratchet, gliding joint, hinge joint, anchored pivot, and the like. The in vitro analyte test strip contacting portion 40 may be pivotally mounted to other meter portion 60 to allow in vitro analyte test strip contacting portion to pivot about a pivot point 52 (for example, shown in FIG. 2) through a wide range of angled motion. Connector 50 thus defines a pivot axis about which in vitro analyte test strip contacting portion 40 pivots.

Connector 50 may include a movement lock or otherwise resist movement (gravity resistant), unless a force is applied thereto (or the movement lock is unlocked) to move it. In this manner, in vitro analyte test strip contacting portion 40 may be locked in place in any of a plurality of selectable positions. For example, in certain embodiments, when connector 50 is caused to move, an engaged locking mechanism may be disengaged to allow uninhibited movement of the in vitro analyte test strip contacting portion, and re-engaged to lock the in vitro analyte test strip contacting portion in a selected position. A locking mechanism or the movement lock coupled to connector 50 may be engaged/disengaged simply by application of a small force to in vitro analyte test strip contacting portion 40 to move it in a direction (e.g., a light urging such as a push from a finger), or an active locking mechanism may include a user interface (e.g., button, latch, or the like) that may be engageable and actuated by a user to lock and unlock the in vitro analyte test strip contacting portion.

FIGS. 2 and 3 show side views of meter 10. FIG. 2 shows in vitro analyte test strip contacting portion 40 in a first position relative to second portion 60/reporting module 62 such that in vitro test strip port 42 of the meter 10 is substantially aligned with longitudinal axis L1, but pivotable about connector 50 through a range of motion relative to an axis such as a long axis L1 (if so definable by the meter 10 or meter portion 60) where the in vitro analyte test strip port 42 may pivot through an angle alpha ($\alpha$), e.g., that may range from about −90 degrees to about +90 degrees relative to the longitudinal axis L1 of the meter 10 and/or meter portion 60 (that is, for example, the pivoting angle alpha ($\alpha$) defining a range of approximately 180 degrees). This motion moves the in vitro analyte test strip port 42 towards or away from the user interface side 66 of the meter 10. FIG. 3 shows moveable in vitro analyte test strip head (in vitro analyte test strip contacting portion) 40 pivoted away from reporting module 62 and towards opposing side 68 such that it is rotated about connector 50 to a second position that enables easy viewing access to reporting module 62 while testing. Although it is shown in FIG. 3 a pivoting angle defining a range of approximately ±90 degrees relative to the longitudinal axis L1 of the meter 10, it is to be understood that in other embodiments, the analyte test strip contacting portion 40 may pivot a range greater than ±90 degrees relative to the longitudinal axis L1 of the meter 10 (that is, for example, the pivoting angle may be defined over a range greater than a total of 180 degrees, such as, a range of approximately 270 degrees or greater). Alternatively, the meter 10 may be configured such that the analyte test strip contacting portion 40 may have a limited pivot range, such as approximately ±45 degrees or less relative to the longitudinal axis L1 of the meter 10.

FIG. 4 shows a perspective view of the meter 10 of FIG. 3 with in vitro analyte test strip 80 being contacted with the in vitro analyte test strip contacting area 42 of meter 10 while in the bent/pivoted position relative to second portion 60 of the meter 10, making it easier for a user to contact the blood sample with the test strip and view results on display 62 at the same time, i.e., without having to re-orient the meter 10.

In a further aspect, the meter 10 may be configured with programming to automatically detect the orientation of the housing 20 such that the orientation of the displayed information is adjusted automatically (or is user settable, configurable or programmable). That is, in one embodiment, the orientation of the output display on the reporting module 62 may be programmed to adjust or automatically adjust to be reoriented based on the orientation of the housing 20 of the meter 10. For example, the numerical display representing the results of the testing (glucose value) on the reporting module 62 may be oriented in a predetermined position relative to the one or more user function selectors 64 on the housing 20 of the meter 10, depending upon the detected or positioned orientation of the second portion 60 of the meter 10 relative to the testing position of the meter 10, or relative to the pivotable in vitro analyte test strip contacting portion 40, or both. In this manner, in one aspect, the output display on the reporting module 62 may be upside down, right side up, inverted, angled (for example, at about 90 degrees relative to the plane defined by, for example, analyte test strip 80 insertion direction towards the in vitro analyte test strip port 42.

In one embodiment, meter 10 also includes a controller module (not shown) coupled to housing 20. The controller module includes hardware and software to perform and control the analyte testing functions, e.g., apply a potential to the in vitro analyte test strip, etc., and process a signal received from in vitro analyte test strip 80 to determine the presence and/or level of concentration of the analyte based on the received signal.

The controller module includes programming to process a signal received from an in vitro analyte test strip and determine a concentration of analyte, e.g., glucose, based on the signal. Details relating to the receipt of an analyte signal from an in vitro analyte test strip and the determination of a concentration of analyte are described, for example, in patents and patent applications described herein, and U.S. Pat. No. 7,041,468, the disclosure of which is incorporated by reference herein. In some embodiments, the analyte meter 10 includes a data storage unit (not shown) coupled to the controller module.

Any suitable in vitro analyte testers may be employed with the meters described herein. In vitro tests strips that may be employed include but are not limited to those described in U.S. Pat. Nos. 6,281,006; 6,103,033; 6,338,790; 6,120,676; 6,143,164, and U.S. patent application Ser. Nos. 11/225,659, now U.S. Pat. No. 8,298,389; Ser. No. 11/237,447, now U.S. Pat. No. 7,846,311; and Ser. No. 11/277,931, now U.S. Pat. No. 7,887,682, the disclosures of which are herein incorporated by reference. In vitro analyte test strips include, but are not limited to FreeStyle® test strips and Precision® analyte test strips from Abbott Diabetes Care Inc.

In certain embodiments, in vitro analyte test strips 80 and in vitro analyte meters 10 may be configured for orientation non-specific insertion of an in vitro analyte test strip into analyte meter 10. By orientation non-specific insertion, it is meant that either the first substrate or the second substrate can be upward facing when the proximal end of in vitro analyte test strip 80 is inserted into the in vitro analyte test strip port of a corresponding analyte meter. That is, either a first substrate or a second substrate of an in vitro analyte test strip can be upward facing when the proximal end of the in vitro analyte test strip is inserted into analyte meter 10. As such, orientation-non specific systems include in vitro analyte test strips that can be inserted in either of the above orientations into a meter described herein without negatively affecting the results of the assay.

A variety of analytes can be detected and quantified using the disclosed in vitro analyte test strips and meters. Analytes of particular interest include glucose and lactate. Additional analytes that may be determined include, for example, acetyl choline, amylase, bilirubin, cholesterol, chorionic gonadotropin, creatine kinase (e.g., CK-MB), creatine, DNA, fructosamine, glucose, glutamine, growth hormones, hormones, ketones (e.g., ketone bodies), lactate, oxygen, peroxide, prostate-specific antigen, prothrombin, RNA, thyroid stimulating hormone, and troponin. The concentration of drugs, such as, for example, antibiotics (e.g., gentamicin, vancomycin, and the like), digitoxin, digoxin, drugs of abuse, theophylline, and warfarin, may also be determined. Assays suitable for determining the concentration of DNA and/or RNA are disclosed in U.S. Pat. No. 6,281,006 and U.S. Pat. No. 6,638,716, the disclosures of each of which are incorporated by reference herein.

The analyte meters described herein find use in methods for determining the concentration of an analyte in a fluid sample from a subject. Generally, these methods include inserting an in vitro analyte test strip into an analyte meter, contacting a fluid sample e.g. blood sample, interstitial fluid, sweat, tears, and the like, with the in vitro analyte in vitro analyte test strip, generating a sensor signal at the working electrode, and determining the concentration of the analyte using the generated sensor signal. Examples of certain electrochemical reactions which can be utilized to produce a sensor signal are described in detail in U.S. Pat. No. 6,592,745, the disclosure of which is incorporated by reference herein. In one embodiment, the determining step includes determining the concentration of the analyte based on amperometry, coulometry, potentiometry, and/or voltametry, including square wave voltametry, or optical techniques, using the analyte test strip. Optical analyte systems are also contemplated.

Certain embodiments may include a medication dosage determination function. For example, where the analyte is glucose, the medication dosage determination function may include a routine in which the controller module performs an algorithm to determine an insulin dose, e.g., a bolus insulin dose, based on the concentration of glucose in the sample. In another embodiment, the medication dosage determination function may be incorporated with an administering routine wherein a medication dose, e.g., an insulin dose, determined according to the dosage determination function described above is administered to the subject via a medication delivery device, e.g., a needle, syringe, external infusion device such as an ambulatory pump, an implantable pump, catheter, inhaler, transdermal patch, or one or more combinations thereof. In another embodiment, the administering routine includes administering a medication dose, e.g., an insulin dose, determined according to the medication dosage determination function to the subject via a medication delivery device positioned at a distance from the analyte meter and in communication with the analyte meter. Further, the determined medication dose, e.g., a bolus dose, may be displayed to the user via optional display unit 62 of analyte meter 10.

In certain embodiments, the controller module includes programming to perform medication dosage calculation functions, such as a single-dose calculation function for injection of, e.g., rapid acting insulin and/or long acting insulin. Analyte meters which include medication dosage calculation functions and methods of performing the dosage calculation functions are described, for example, in U.S. application Ser. Nos. 11/396,182, now U.S. Pat. No. 8,226,891, and 61/149,989, the disclosures of which are incorporated by reference herein. In one embodiment, the controller module is configured to perform a bolus calculation function. For example, the controller module may be configured to determine a bolus dosage, e.g., an insulin bolus dosage, based on the signal received from the analyte test strip. In one embodiment the controller module is configured to perform an algorithm to determine a medication dosage based on a determined concentration of analyte. The in vitro analyte meter 10 may be programmed to automatically enter into a medication dosage calculation mode to, for example, calculate and/or select a medication dosage amount based on information stored in the analyte meter 10 (such as the patient's insulin sensitivity, for example), and/or prompt the patient to provide additional information, such as the amount of carbohydrate to be ingested by the patient for determination of, for example, a carbohydrate bolus dosage determination. In another embodiment, the analyte meter 10 may be programmed to prompt the user to select whether to retrieve a predetermined or preprogrammed medication dosage amount such as, for example, a correction bolus or a carbohydrate bolus, following the display of the determined analyte concentration from an in vitro analyte test strip. In this manner, in one embodiment of the present disclosure, analyte meter 10 may be configured to automatically prompt a user to select whether a medication dosage determination is desired following analyte testing using an in vitro analyte test strip.

In certain embodiments, analyte meter 10 includes an optional medication delivery device or system (not shown), e.g., coupled therewith. Additional information regarding medication delivery devices or systems, such as, for example, integrated systems, is provided, for example, in U.S. Patent Application Publication No. US2006/0224141, published on Oct. 5, 2006, titled "Method and System for Providing Integrated Medication Infusion and Analyte Monitoring System", and U.S. Patent Application Publication No. US2004/0254434, published on Dec. 16, 2004, titled "Glucose Measuring Module and Insulin Pump Combination," the disclosure of each of which is incorporated by reference herein. Medication delivery devices which may be provided with analyte meter 10 include, e.g., a needle, syringe, pump, catheter, inhaler, transdermal patch, injection pen, and the like, or combinations thereof. For example, a medication delivery device or system may be in the form of a drug delivery injection pen such as a pen-type injection device incorporated within housing 20 of analyte meter 10, or as part of an in vivo integrated system such as may be incorporated into a component of system 100 (e.g., integrated with control unit 220 and/or mounting unit 24 and/or housing 120. Additional information is provided in U.S. Pat. Nos. 5,536,249 and 5,925,021, the disclosures of each of which are incorporated by reference herein.

The medication delivery system may be used for injecting a dose of medication, such as insulin, into a patient based on a prescribed medication dosage, and may be automatically updated with dosage information received from the controller module of analyte meter 10. In another embodiment, the medication dosage of the medication delivery system may include manual entry of dosage changes made through, for example, optional input 64 coupled to the housing 20 of analyte meter 10. Medication dosage information associated with the medication delivery system may be displayed on an optional display unit 62 disposed on housing 20 of analyte meter 10.

Analyte meter 10 may be a component of one or more analyte detection systems. For example, an analyte detection system according to the present disclosure may include analyte meter 10 or integrated system 100 as described herein (see, for example, FIG. 5) in addition to one or more sample acquisition and/or testing elements. In one embodiment, an analyte detection system according to the present disclosure includes an in vitro analyte test strip, e.g., an in vitro analyte test strip and a lancet.

In some embodiments, a lancet and an in vitro analyte test strip are receivable into the housing of the analyte meter 10. In other embodiments, the lancet and the test strip are not integrated into the housing of the analyte meter 10, but are instead included in the system as separate components.

Where the test strip is integrated into the housing of an analyte meter 10, the housing may be configured to hold one or more cartridges or magazines containing test strips to be used in the operation of the system. Similarly, where the lancet is integrated into the housing of an analyte meter 10, the housing may be configured to hold one or more cartridges or magazine containing lancets to be used in the operation of the system.

Additional systems incorporating the analyte meters described herein will be readily apparent to those of ordinary skill in the art upon reading the present disclosure.

In some embodiments, the analyte meter 10 includes an optional communication device (not shown), e.g., a receiver and/or transmitter for communicating with another device, e.g., a medication delivery device and/or a personal computing system (PC, notebook, laptop, etc. mobile phone, PDA, e.g., using a health management system such as the CoPilot™ system available from Abbott Diabetes Care Inc., Alameda, Calif. The communication device may be configured for wired or wireless communication, including, but not limited to, radio frequency (RF) communication, Zigbee® communication protocols, WiFi, Bluetooth® communication protocols, and cellular communication, such as code division multiple access (CDMA) or Global System for Mobile (GSM) communications.

In one embodiment, analyte meter 10 includes a wireless communication device, wherein the wireless communication device is configured for bi-directional radio frequency (RF) communication with other devices to transmit and/or receive data to and from the analyte meter 10. In one embodiment, the communication device is configured to include physical ports or interfaces such as a USB port, an RS-232 port, or any other suitable electrical connection port to allow data communication between the analyte meter 10 and other external devices such as a computer terminal (for example, at a user's home, physician's office or in hospital environment), an external medical device, such as an infusion device or including an insulin delivery device, or other devices that are configured for similar complementary data communication. In one embodiment, the communication device is configured for infrared communication, Bluetooth® communication, or any other suitable wireless communication mechanism to enable the analyte meter 10 for communication with other devices such as infusion devices, analyte monitoring devices, computer terminals and/or networks, communication enabled mobile telephones, personal digital assistants, or any other communication devices which the patient or user of the analyte meter may use in conjunction therewith, in managing the treatment of a health condition, such as diabetes.

In one embodiment, the analyte meter is configured to wirelessly communicate with a server device, e.g., using a common standard such as 802.11 or Bluetooth® RF protocol, or an IrDA infrared protocol. The server device may include another portable device, such as a Personal Digital Assistant (PDA) or notebook computer, or a larger device such as a desktop computer, appliance, etc. In some embodiments, the server device has a display, such as a liquid crystal display (LCD), as well as an input device, such as buttons, a keyboard, mouse or touch-screen. With such an arrangement, the user may control the meter indirectly by interacting with the user interface(s) of the server device, which in turn interacts with the meter across a wireless link.

In certain embodiments, the in vitro meters described herein may be combined with in vivo analyte testing systems to provide an integrated system. Embodiments include in vitro blood glucose meters having moveable in vitro analyte test strip contacting portions as part of, including coupled to, e.g., integrated with, an in vivo analyte testing system. In vivo systems include an in vivo analyte sensor that is configured to be at least partially implanted in a user—in contact with biological fluid—for a period of time, to test for analyte in the contacted biological fluid continuously or semi-continuously over the period of time. Over the period of time of in vivo testing, the in vivo periodic testing may be used in conjunction with in vitro testing. For example, analyte results obtained from in vitro testing may be used to calibrate an in vivo system and/or may be used to confirm results of an in vivo system, e.g., prior to relying on the results obtained by the in vivo analyte system. The in vitro meters described herein that include an articulating portion, may be integrated into a housing of a component of an in vivo system, e.g., integrated into a housing of an in vivo sensor control unit, an in vivo receiver unit, an in vivo mounting unit, and/or other. Integrated in vivo and in vitro analyte systems are described, e.g., in U.S. Pat. Nos. 5,262,035; 5,264,104; 5,262,305; 5,320,715; 5,593,852; 6,175,752; 6,560,471; 6,746, 582, 7,299,082 and in U.S. patent application Ser. No. 10/745,878 filed Dec. 26, 2003, now U.S. Pat. No. 7,811,231, entitled "Continuous Glucose Monitoring System and Methods of Use", each of which is incorporated herein by reference.

Figure 5:
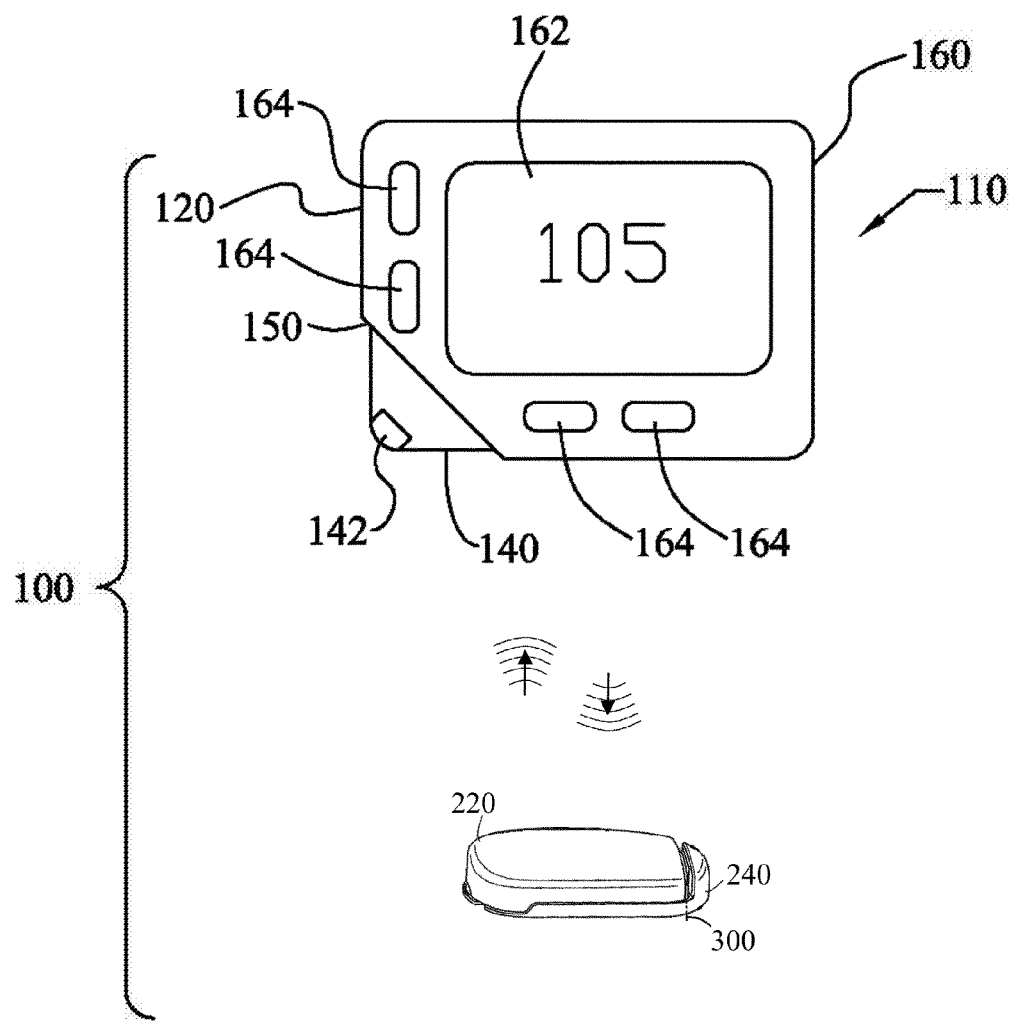
FIG. 5 shows a frontal view of an embodiment of an in vivo analyte testing system that includes an in vivo analyte sensor, an in vivo sensor control unit, optional mounting unit for the in vivo sensor control unit and a receiver module, and an adjustable in vitro analyte meter according to the present disclosure that is integrated into a housing of the in vivo analyte testing system and the meter has a portion that is moveable relative to at least one other portion of the integrated housing such as a reporting module portion.

FIG. 5 shows an integrated analyte system 100 in which an in vitro analyte meter having a moveable in vitro analyte test strip contacting portion is also a component of an in vivo system, and specifically in this embodiment a receiver unit of an in vivo analyte system is integrated with an in vitro meter as described herein.

The integrated system 100 of FIG. 5 includes an in vivo analyte sensor 300, an in vivo sensor control unit 220, and optional mounting unit 240 that mates with the in vivo sensor control unit 220, and a receiver unit 110 to receive signals from and/or send signals to the sensor control unit, including signals related to the detection of an analyte by in vivo sensor 300. Receiver unit 110 includes a housing 120 having a first portion or sensor contacting portion 140, and at least one other portion 160, coupled together by connector 150. First portion 140 includes an in vitro analyte test strip contacting area 142 to make contact (electrical and/or mechanical) with an in vitro analyte test strip. The in vitro analyte test strip contacting portion 140 and in vitro analyte test strip contacting area 142 function analogously to the in vitro analyte test strip contacting portion 40 and in vitro analyte test strip contacting area 42 of FIGS. 1-4.

In certain embodiments, the second portion 160 of receiver 110 includes optional reporting module 162 to report results of an analyte test to a user on a frontal or user interface side, which is opposite to an opposing side. Reporting module 162 may include audible and/or visual components and in certain embodiments may include a voice user interface. In certain embodiments, one or more user function selector(s) 164 may be included. User function selector(s) 164 may include, but are not limited to, one or more buttons, a jog wheel, capacitive sensing slider inputs, keypad, and the like, or a combination thereof. In certain embodiments, some or all of the one or more user function selector(s) 164 may control aspects related to the in vivo analyte monitoring system, the integrated in vitro analyte monitoring system, or a combination thereof. Some or all of the user function selector(s) 164 may be soft keys and may control multiple functions as described above in conjunction with FIGS. 1-3.

FIGS. 6 and 7 show side views of receiver unit 110. FIG. 6 shows in vitro analyte test strip contacting portion 140 in a first position relative to the other portion 160 such that the angle beta (β) between first portion 140 and user interface side of the second portion 160 is substantially +90 degrees and −90 degrees relative to the receiver unit 110 axis L3 defined by the dotted line shown in the figure (that is, approximately 180 degrees of rotation shown along the angle beta (β)). FIG. 7 shows in vitro analyte test strip contacting portion 140 rotated about pivot point 152 at connector 150 in a downward position to a second position. In this particular exemplary figure, in vitro analyte test strip head 140 is shown pivoted at various angles from about a −90 degree right angle to a +90 degree right angle to the housing. FIG. 8 shows a perspective view of receiver unit 110 of FIG. 7 with the in vitro analyte test strip contacting area pivoted in downward position to a second position relative to housing 160, and with an in vitro analyte test strip 80 being contacted with the in vitro analyte test strip contacting area 142. In this manner, analyte testing is facilitated by the downward pivot of the in vitro analyte test strip contacting area 142 because the user is able to contact sample with the test strip and view the results on display 162 simultaneously without having to re-orient the receiver unit 110.

Accordingly, as described herein embodiments include in vitro glucose meters for contacting an in vitro glucose test strip and providing the presence and/or concentration of glucose from a sample applied to the in vitro glucose test strip. Embodiments include meters having an in vitro glucose test strip contacting portion pivotally mounted to a user interface portion of the meter so that the in vitro test strip contacting portion is selectively pivotable relative to the user interface portion. An in vitro glucose test strip contacting portion may be pivotable towards the user interface portion and/or away from the user interface portion, e.g., towards and/or away from a reporting module of a user interface portion. A reporting module may be an audio and/or visual reporting module, e.g., a visual display.

An in vitro glucose test strip contacting portion may be pivotable to provide an angle of about 90 degrees relative to the user interface portion, e.g., towards and/or away from the user interface portion.

An in vitro test strip contacting portion may include an in vitro glucose test strip port.

An in vitro glucose test strip contacting portion may pivot through a range of about 180 degrees e.g., without the corresponding movement of a user interface portion.

A meter may include a lock to lock the in vitro glucose test strip contacting portion in a position throughout the range.

An in vitro glucose meter may be integrated with an in vivo glucose monitoring system.

Embodiments include methods of glucose monitoring. Methods may include selectively moving an in vitro glucose test strip contacting portion of an in vitro glucose meter relative to a user interface portion of the meter; contacting an in vitro glucose test strip to the in vitro glucose test strip contacting portion; applying a biological sample to the in vitro test strip; and obtaining information about glucose from the user interface portion of the meter.

Methods may include moving the in vitro glucose test strip contacting portion towards and/or away from a user interface portion, e.g., towards and/or away from a reporting module of a user interface portion. Methods may include moving an in vitro glucose test strip contacting portion to provide an angle of about 90 degrees relative to the user interface portion of a meter.

Methods may include moving an in vitro glucose test strip contacting portion through a range of about 180 degrees, e.g., without the corresponding movement of a user interface portion.

Methods may include locking the in vitro glucose test strip contacting portion in a position throughout the range.

Methods may include integrating in vitro glucose meter with an in vivo glucose monitoring system, and obtaining glucose information from in vivo glucose monitoring and from in vitro monitoring.

Methods of glucose testing may also include lancing a test area to express biological fluid from the target area; contacting an in vitro glucose test strip coupled to an in vitro glucose meter to the expressed biological fluid at the target area; and pivoting a display portion of the glucose meter without substantially moving the test strip from the target area so that the display is viewable while the contacting occurs.

Embodiments include integrated glucose monitoring systems. The integrated system may include an in vivo glucose sensor for in vivo glucose testing; an in vitro glucose test strip for ex vivo glucose testing; one or more processors for processing glucose information from the in vivo sensor and the in vitro sensor; and a housing comprising an in vitro analyte test strip contacting portion pivotal relative to a user interface portion of the meter, the housing comprising a user interface to report the processed glucose information obtained from the in vivo sensor when positioned in a user and the in vitro glucose test strip when contacted with the in vitro glucose test strip contacting portion.

While the present disclosure has been described with reference to the specific embodiments thereof, it should be understood by those skilled in the art that various changes may be made and equivalents may be substituted without departing from the true spirit and scope of the present disclosure. In addition, many modifications may be made to adapt a particular situation, material, composition of matter, process, process step or steps, to the objective, spirit and scope of the present disclosure. All such modifications are intended to be within the scope of the claims appended hereto.

What is claimed is:

1. An in vitro glucose meter, comprising:
 a housing including a user interface portion, the housing further including an in vitro glucose test strip contacting portion pivotally mounted to the user interface portion of the housing so that the in vitro glucose test strip contacting portion is selectively pivotable relative to the user interface portion, wherein the in vitro glucose test strip contacting portion pivots through a range of about 180 degrees, and further comprising a lock to substantially fix the in vitro glucose test strip contacting portion in a position throughout the range.

2. The meter of claim 1, wherein the in vitro glucose test strip contacting portion is pivotable towards a reporting module of the user interface portion.

3. The meter of claim 2, wherein the reporting module comprises a display.

4. The meter of claim 1, wherein the in vitro glucose test strip contacting portion is pivotable away from a reporting module of the user interface portion.

5. The meter of claim 4, wherein the reporting module comprises a display.

6. The meter of claim 1, wherein the in vitro glucose test strip contacting portion is pivotable to provide an angle of about 90 degrees relative to the user interface portion.

7. The meter of claim 1, wherein the in vitro glucose test strip contacting portion comprises an in vitro glucose test strip port that is pivotally mounted to the user interface portion of the housing.

8. The meter of claim 1, further including an in vivo glucose monitoring system integrated in the housing.

9. A method, comprising:
 selectively moving an in vitro glucose test strip contacting portion of an in vitro glucose meter relative to a user interface portion of the meter;
 contacting an in vitro glucose test strip to the in vitro glucose test strip contacting portion;
 applying a biological sample to the in vitro glucose test strip; and
 obtaining information about glucose from the user interface portion of the meter;
  wherein the in vitro glucose meter includes a housing, the housing further including the in vitro glucose test strip contacting portion pivotally mounted to the user interface portion so that the in vitro glucose test strip contacting portion is selectively pivotable relative to the user interface portion, wherein the in vitro glucose test strip contacting portion pivots through a range of about 180 degrees, and further including a lock to substantially fix the in vitro glucose test strip contacting portion in a position throughout the range.

10. The method of claim 9, comprising moving the in vitro glucose test strip contacting portion towards a reporting module of the user interface portion.

11. The method of claim 9, comprising moving the in vitro glucose test strip contacting portion away from a reporting module of the user interface portion.

12. The method of claim 9, comprising moving the in vitro glucose test strip contacting portion to provide an angle of about 90 degrees relative to the user interface portion.

13. The method of claim 12, wherein the in vitro glucose test strip contacting portion is moveable towards the user interface portion.

14. The method of claim 12, wherein the in vitro glucose test strip contacting portion is moveable away from the user interface portion.

15. The method of claim 9, comprising locking the in vitro glucose test strip contacting portion in a position throughout the range.

16. The method of claim 9, further comprises obtaining glucose information from in vivo glucose monitoring and from in vitro monitoring.

17. An integrated glucose monitoring system, comprising:
an in vivo glucose sensor for in vivo glucose testing;
an in vitro glucose test strip for ex vivo glucose testing;
one or more processors for processing glucose information from the in vivo glucose sensor and the in vitro glucose test strip; and
a housing including a user interface portion, the housing further including an in vitro glucose test strip contacting portion pivotally mounted to the user interface portion of the housing so that the in vitro glucose test strip contacting portion is selectively pivotable relative to the user interface portion, wherein the in vitro glucose test strip contacting portion pivots through a range of about 180 degrees, and further including a lock to substantially fix the in vitro glucose test strip contacting portion in a position throughout the range.

18. A method, comprising:
lancing a test area to express biological fluid from a target area;
contacting an in vitro glucose test strip coupled to an in vitro glucose meter to the expressed biological fluid at the target area; and
pivoting a display portion of the in vitro glucose meter without substantially moving the in vitro glucose test strip from the target area so that the display portion is viewable while the in vitro glucose test strip is contacting the expressed biological fluid;
wherein the in vitro glucose meter includes a housing, the housing further including an in vitro glucose test strip contacting portion pivotally mounted to the display portion so that the in vitro glucose test strip contacting portion is selectively pivotable relative to the display portion, wherein the in vitro glucose test strip contacting portion pivots through a range of about 180 degrees, and further including a lock to substantially fix the in vitro glucose test strip contacting portion in a position throughout the range.

* * * * *